(12) United States Patent
Gyuris

(10) Patent No.: US 6,342,356 B1
(45) Date of Patent: Jan. 29, 2002

(54) METHODS AND REGENTS FOR IDENTIFYING SYNTHETIC GENETIC ELEMENTS

(75) Inventor: Jeno Gyuris, Winchester, MA (US)

(73) Assignee: GPC Biotech, Inc., Waltham, MA (US)

(*) Notice: Subject to any disclaimer, the term of this patent is extended or adjusted under 35 U.S.C. 154(b) by 0 days.

(21) Appl. No.: 09/522,728

(22) Filed: Mar. 10, 2000

Related U.S. Application Data

(60) Provisional application No. 60/123,924, filed on Mar. 12, 1999.

(51) Int. Cl.$^7$ .......................... C12Q 1/68; C12P 21/06; C12P 19/34; C12N 5/00; C07H 21/04
(52) U.S. Cl. ........................ 435/6; 435/69.1; 435/91.1; 435/375; 435/455; 536/23.1; 536/23.5; 536/24.5
(58) Field of Search .......................... 435/6, 69.1, 91.1, 435/91.5, 455, 325, 375; 514/44; 536/23.1, 24.5, 23.5

(56) References Cited

U.S. PATENT DOCUMENTS

| | | |
|---|---|---|
| 4,868,116 A | 9/1989 | Morgan et al. |
| 4,980,286 A | 12/1990 | Morgan et al. |
| 5,174,996 A | 12/1992 | Weber et al. |
| 5,206,352 A | 4/1993 | Roninson et al. |
| 5,256,775 A | 10/1993 | Froehler |
| 5,264,574 A | 11/1993 | Carroll et al. |
| 5,283,317 A | 2/1994 | Saifer et al. |
| 5,580,736 A | 12/1996 | Brent et al. |
| 5,695,941 A | 12/1997 | Brent et al. |
| 5,753,432 A | 5/1998 | Gudkov et al. |
| 5,759,776 A * | 6/1998 | Smith et al. .................... 435/6 |
| 5,846,721 A | 12/1998 | Soares et al. |
| 5,955,275 A * | 9/1999 | Kamb ........................... 435/6 |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 92/07071 | 4/1992 |
| WO | WO 92/07573 | 5/1992 |
| WO | WO 94/20618 | 9/1994 |
| WO | WO 95/253855 | 9/1995 |
| WO | WO 95/34680 | 12/1995 |
| WO | WO 97/27212 | 7/1997 |
| WO | WO 98/12339 | 3/1998 |
| WO | WO 98/21366 | 5/1998 |
| WO | WO 99/32618 | 7/1999 |
| WO | WO 99/47643 | 9/1999 |
| WO | WO 99/53098 | 10/1999 |

OTHER PUBLICATIONS

Thomson et al. "Embryonic Stem Cell Lines Dervied from Human Blastocysts." *Science*, 282: 1145 (1998).

Shamblott et al. "Derivation of luripotent stem cells from cultured human primordial germ cells." *PNAS*, 95: 13726 (1998).

Palazzolo and Meyerowitz. "A family of phage cDNA cloning vectors, delta–SWAJ, allowing the amplification of RNA sequences." *Gene*, 52:197–206 (1987).

Palazzolo et al. "Use of a New Strategy to Isolate and Characterize 436 Drosophila cDNA Clones Corresponding to RNAs Detected in Adult Heads but Not in Early Embryos." *Neuron*, 3:527 (1989).

Palazzolo et al. "Phage Iambda cDNA cloning vectors for subtractive hybridization, fusion–protein synthesis and Cre–IoxP automatic plasmid subcloning." *Gene*, 88:25 (1990).

Meissner et al. "Bacteriophage Delta cloning system for the construction of directional cDNA libraries." *PNAS*, 84:4171 (1987).

Beutler et al. "Gamma–Glutamylcystein Synthetase Deficiency and Hemolytic Anemia." *Blood*, 76:271 (1990).

Eglitis et al. "Gene expression in mice after high efficiency retroviral–mediated gene transfer." *Science*, 230: 1395–1398 (1985).

Danos and Mulligan. "Safe and efficient generation of recombinant retroviruses with amphotropic and ecotropic host ranges." *Proc. Natl. Acad. Sci. USA*, 85:6460–6464 (1988).

Wilson et al. "Retrovirus–mediated transduction of adult hepatocytes." *Proc. Natl. Acad. Sci. USA*, 85:3014–3018 (1988).

Armentano et al. "Expression of human factor IX in rabbit hepatocytes by retrovirus–mediated gene transfer: Potential for gene therapy of hemophilia B." *Proc. Natl. Acad. Sci. USA*, 87: 6141–6145 (1990).

Huber et al. "Retroviral–mediated gene therapy for the treatment of hepatocellular carcinoma: an innovative approach for cancer therapy" *Proc. Natl. Acad. Sci. USA*, 88:8039–8043 (1991).

Chowdhury et al.; "Long Term Improvement of Hypercholesterolemia After ex Vivo Gene Therapy in LDLR–Deficient Rabbits", *Science* 254: 1802=1805 (1990).

(List continued on next page.)

*Primary Examiner*—Andrew Wang
*Assistant Examiner*—Jane Zara
(74) *Attorney, Agent, or Firm*—Matthew P. Vincent; David P. Halstead; Ropes & Gray

(57) ABSTRACT

The present invention relates to a selection method that allows fast recovery and identification of functional gene fragments which selectively inhibit growth, e.g., are cytostatic or cytotoxic, of particular cell-types, such as transformed cells. The strategy relies, in part, on the ability of small gene fragments to encode dominant-acting synthetic genetic elements (SGEs), e.g., molecules which interfere with the function of genes from which they are derived. SGEs which can be identified by the subject method include, but are not limited to, inhibitory antisense RNA molecules, ribozymes, nucleic acid decoys, and small peptides.

36 Claims, 10 Drawing Sheets

OTHER PUBLICATIONS van Beusechem et al. "Long–term expression of human adenosine deaminase in rhesus monkeys transplanted with retrovirus–infected bone–marrow cells." *Proc. Natl. Acad. Sci. USA*, 89: 7640–7644 (1992).

Kay et al. "Hepatic Gene Therapy: Persistent Expression of Human alpha1–Antitrypsin in Mic after Direct Gene Delivery In Vivo." *Human Gene Therapy*, 3:641–647 (1992).

Dai et al.; "Gene Therapy Via Primary Myoblasts: Long–Term Expression of Factor IX Protein Following Transplantation in Vivo", *Proc. Natl. Acad. Sci. USA*, 89: 10892–10895 (1992).

Hwu et al. "Functional and Molecular Characterization of Tumor–Infiltrating Lymphocytes Transduced with Tumor Necrosis Factor–alpha cDNA for the Gene Therapy of Cancer in Humans." *J. Immunol.* 150:4104–4115 (1993).

Keown et aL.; "Methods for Introducing DNA into Mammalian Cells", *Methods in Enymol.* 185:527–536 (1990).

Alton and Vapnek. "Nucleotide sequence analysis of chloramphenicol resistance tranposon Tn9." *Nature*, 282:864–869 (1979).

DeWet et al. "Firefly Luciferase gene: structure and expression in mammalian cells." *Mol. Cell Biol.*, 7:725–737 (1987).

Engebrecht and Silverman. "Identification of genes and gene products necessary for bacterial bioluminescence." *PNAS*, 1:4154–4158 (1984).

Baldwin et al. "Cloning of the Luciferase Structural Genes from *Vibrio harveyi* and Expression of Bioluminescence in *Escherichia coli*." *Biochemistry*, 23:36631984).

Toh et al. "Isolation and characterization of a rat liver alkaline pohsphate gene." *Eur. J. Biochem.*, 23:3663–3667 (1989).

Cullen and Malim,; "Secreted Placental Alkaline Phosphatase as a Eukaryotic Reporter Gene", *Methods in Enzymol.*, 216:362–368 (1992).

Sheng et al. "The regulation and function of c–fos and other immediate early genes in the nervous system." *Neuron*, 4:477–485 (1990).

Fink et al. "The CGTCA sequence motif is essential for biological activity of vasoactive intestinal peptide gene cAMP–regulated enhancer." *Proc. Natl. Acad. Sci.*, 85:6662–6666 (1988).

Montiminy et al. "Identification of a cyclic–AMP–responsive element within the rat somatostatin gene." *Proc. Natl. Acad. Sci*, 8.3:6682–6686 (1986).

Comb et al. "A cyclic AMP– and phorbol ester–inducible DNA element." *Nature*, 323:353–356 (1986).

Short et al. "Characterization of the Phosphenolpyruvate Carboxykinase (GTP) Promoters–regulatory Region." *J. Biol. Chem.*, 261:9721–9726 (1986).

Changelian et al. "Structure of the NGFI–A gene and detection of upstream sequences for its transcriptional induction by nerve growth factor." *Proc. Natl. Acad. Sci.*, 86:377–381 (1989).

Packard et al. "Profluorescent protease substrates: Intramolecular dimers described by the exciton model." *Proc. Natl. Acad. Sci.*, 93:11640–11645 (1996).

Habig et al. "Glutathione S–Tranferases." *J. Biol. Chem.*, 249: 7130 (1974).

Ellison et al."Epitope–tagged Ubiquitin." *J. Biol. Chem.*, 266:21150–21157 (1991).

Bear et al. "Purification and Functional Reconstitution of the Cystic Fibrosis Transmembrane Conductance Regulator (CFTR)." *Cell*, 68: 809–818 (1992).

Newton et al. "Transfer of Band 3, the Erythrocyte Anion Transporter, between Phospholipid Vesicles and Cells." *Biochemistry*, 22:6110–6117 (1983).

Reber et al. "Hydrophobic Properties of the Beta–1 and Beta–2 Subunites of the Rat Brain Sodium Channel." *J. Biol. Chem.* 262: 11369–11374 (1987).

Borle. "An overview of techniques for the measurement of calcium distribution, calcium fluxes, and cytosolic free calcium in mammalian cells." *Environmental Health Perspectives*, 84:45–50 (1990).

Lyons and Nelson. "An immunological method for detecting gene expression in yeast colonies." *PNAS*, 81:7426–7430 (1984).

Zervos et al. "Mxi1, a Protein That Specifically Interacts with Max to Bind Myc–Max Recognition Sites." *Cell*, 72:223–232 (1993).

Madura et al. "N–recognin/Ubc2 Interactions in the N–end Rule Pathway." *J. Biol. Chemistry*, 268:12046–12054 (1993).

Bartel et al. "Elimination of False Positives That Arise in Using the Two–Hybrid System." *Biotechniques*, 14:920–924 (1993).

Iwabuchi et al. "Use of the two hybrid system to identify the domain of p53 involved in oligomerization." *Oncogene*, 8:1693–1696 (1993).

Ruf et al. "Mutational Mapping of Functional Residues in Tissue Factor: Identification of Factor VII Recognition Determinants in Both Structural Modules of the Predicted Cytokine Receptor Homology Domain." *Biochemistry*, 222:1565–1572 (1994).

Wang et al. "Single Amino Acid Insertions Probe the a Subunit of the *Escherichia coli* F1F0–ATP Synthase" *J. Biol. Chem.*, 269:3095–3099 (1994).

Balint et al. "Antibody engineering by parsimonious mutagenesis." *Gene*, 137: 109–118 (1993).

Grodberg et al. "Alanine scanning mutagenesis of human erythropoietin identifies four amino acids which are critical for biological activity." *Eur. J. Biochem.*, 218:597–601 (1993).

Nagashima et al. "Alanine–scanning Mutagenesis of the Epidermal Growth Factor–like Domains of Human Thrombomodulin Identifies Critical Residues for Its Cofactor Activity." *J. Biol. Chem.*, 268:2888–2892 (1993).

Lowman et al. "Selecting High–Affinity Binding Proteins by Monovalent Phage Display." *Biochemistry*, 30:10832–10838 (1991).

Cunningham et al. "High–resolution epitope mapping of hGH–receptor interactions by alanine–scanning mutagenesis." *Science*, 244:1081–1085 (1989).

Gustin et al. "Characterization of the role of individual protein binding motifs within the hepatitis B virus enhancer I on X promoter activity using linker scanning mutagenesis." *Virology*, 193:653–660 (1993).

Brown et al. "The promoter for the procyclic acidic repetitive proptein (PARP) genes of trypanosoma brucei shares features with RNA polymerase I promoters." *Mol. Cell. Biol.*, 12:2644–2652 (1992).

McKnight et al. "Transcriptional control signals of a eukaryotic protein–coding gene." *Science*, 217:316 (1982).

Myers et al. "Fine structure genetic analysis of a Beta–globin promoter." *Science*, 232:613 (1986).

Fauchere, J. "Elements for the Rational Design of Peptide Drugs." *Adv. Drug Res.*, 15:29–69 (1986).

Evans et al. "Design of nonpeptidal ligands for a peptide receptor: cholecystokinin antagonists." *J. Med. Cehm.*, 30:1229 (1987).

Ewenson et al. "Ketomethylene pseudopeptide analogues of substance P: synthesis and biological activity." *J. Med. Chem.*, 29:295 (1986).

Nagai et al. "Synthesis of a bicyclic dipeptide with the shape of Beta–turn central part." *Tetrahedron Lett*, 26:647 (1985).

Sato et al. "Synthesis and antibiotic activity of a gramacidin S analogue containing bicyclic Beta–turn dipeptides." *J. Chem Soc. Perkin Trans.*, 1:1231 (1986).

Gordon et al. "Design of Peptide Derived Amino Alcohols as Transition–State Analog Inhibitors of Angiotensin Converting Enzyme." *Biochem. Biophys. Res. Commun.*, 126:419 (1985).

Dann et al. "Human Renin: A New Class of Inhibitors." *Biochem. Biophys. Res. Commun.* 134:71–77 (1986).

Van der Krol et al. "Modulation of Eukaryotic Gene Expression by Complementary RNA or DNA Sequences." *Biotechniques*, 6:958–976 (1988).

Stein et al. "Oligodeoxynucleotide as Inhibitors of Gene Expression: A Review." *Cancer Res.*, 48:2659–2668 (1988).

Kuntz. "Structure–based strategies for drug design and discovery." *Science*, 257:1078–1082 (1992).

Dixon. "Computer–aided drug design: getting the best results." *Trends in Biotechnology*, 10:357–363 (1992).

Dunn et al.; "Isolation of Efficient Antivirals: Genetic Suppressor Elements against HIV–1", Gene Therapy 6: 130–137 (1999).

Hensel et al.; "Simultaneous Identification of Bacterial Virulence Genes by Negative Selection", Science 269:400–403 (Jul. 21, 1995).

International Search Report.

* cited by examiner

METHODS AND REGENTS FOR IDENTIFYING SYNTHETIC GENETIC ELEMENTS

This application is based on U.S. Provisional Application No. 60/123,924, filed Mar. 12, 1999, hereby incorporated by reference in its entirety.

BACKGROUND OF THE INVENTION

Functional inactivation of genes through the expression of synthetic genetic elements comprising all or a part of the gene to be inactivated is known in the art. At least four mechanisms exist by which expression of such specific genetic elements can result in inactivation of their corresponding gene. These are interference with protein function by polypeptides comprising nonfunctional or partly nonfunctional analogs of the protein to be inhibited or a portion thereof, interference with mRNA translation by complementary anti-sense RNA or DNA, destruction of mRNA by anti-sense RNA coupled with ribozymes, and interference with mRNA by RNA sequences homologous to a portion of the mRNA representing an important regulatory sequence.

Although gene suppression is quite useful for scientific studies of gene function and holds considerable promise for certain applications in disease therapy and genetic modification of plants and animals, current methods for identifying effective synthetic genetic elements (SGEs) are time consuming and arduous. Interference by dominant negative mutant proteins, for example, either requires extensive knowledge about the functional domain structure of the protein so that reasonably promising candidate mutant proteins can be prepared, or necessitates individual preparation and screening of numerous candidate mutant proteins. Antisense RNA and competitive homologous RNA similarly require extensive individual preparation and screening of candidate inhibitory sequences, absent considerable knowledge about important specific sequences within the RNA.

There is, therefore, a need for generalized methods for identifying and isolating SGEs that will allow simplified determination of effective elements without undue experimentation or extensive structure/function knowledge. An ideal method would allow simultaneous analysis of multiple possible candidate SGEs, regardless of their mechanism of action.

BRIEF SUMMARY OF THE INVENTION

The present invention facilitates drug discovery by providing a method for identifying agents that selectively confer a desired phenotype on a target cell, comprising:

(i) transfecting subtractive cells with a library of expression vectors comprising a variegated population of coding sequences for potential synthetic genetic elements (SGEs);

(ii) isolating those SGE vectors of the SGE library that do confer the desired phenotype, or a phenotype that interferes with the detection thereof, to the subtractive cells;

(iii) transfecting target cells with the sub-population of SGE vectors isolated in step (ii); and (iv) isolating those SGE vectors that confer the desired phenotype to the target cell.

One aspect of the subject method relates to a method for identifying agents with selective antiproliferative activity for a target cell, comprising:

(i) transfecting subtractive cells with a library of expression vectors comprising a variegated population of coding sequences for potential synthetic genetic elements (SGEs);

(ii) isolating those SGE vectors of the SGE library that are not lethal to the subtractive cells;

(iii) transfecting target cells with the non-lethal SGE vectors isolated in step (ii); and (iv) isolating those SGE vectors that are lethal to the target cell.

In preferred embodiments, the method is carried out using target and subtractive cells that are eukaryotic cells, more preferably mammalian cells. In certain embodiments, one or both of the target and subtractive cells are human cells.

In certain embodiments, the target is a transformed cell, and the subtractive cell is an untransformed cell.

In other embodiments, the target is a cell infected with a virus, and the subtractive cell is an uninfected cell.

In preferred embodiments, the expression vectors are viral vectors, and more preferably retroviral vectors.

The SGE library can be generated from a normalized cDNA library, a subtractive cDNA library, or a combination thereof.

By random incorporation, or directional cloning, the library can be generated to include SGE having a sense oriented sequence encoding a peptide, and/or an antisense-oriented sequence encoding an antisense RNA.

Another aspect of the invention relates to formulations of the SGEs identified according to the subject method. For example, the present invention provides a synthetic oligonucleotide having a nucleotide sequence from about 12 nucleotides to all of the nucleotide sequence of an antisense RNA encoded by an SGE identified according to the subject method. In other embodiments, the invention provides an isolated peptide encoded by an SGE identified according to the subject method, or a peptidomimetic thereof.

DETAILED DESCRIPTION OF THE PREFERRED EMBODIMENTS i. Overview

In one aspect, the present invention facilitates drug discovery by providing a method for identifying nucleic acid sequences that confer a desired phenotype in a cell-type selective manner. The strategy relies, in part, on the ability of small gene fragments to encode dominant-acting synthetic genetic elements (SGEs), e.g., molecules that interfere with the function of genes from which they are derived (antagonists) or that are dominant constitutively active fragments (agonists) of such genes. SGEs that can be identified by the subject method include, but are not limited to, polypeptides, inhibitory antisense RNA molecules, ribozymes, nucleic acid decoys, and small peptides.

In addition to being of direct potential therapeutic value, e.g., as a pharmaceutical, an SGE identified by the present invention identifies an endogenous gene that is also of potential diagnostic and other therapeutic value. For instance, a gene whose activity is inactivated by an identified SGE can itself be used as a target for drug development, e.g., to identify other agents, such as small molecules and natural extracts, which can also inhibit the function of the endogenous gene. Thus, another aspect of the present invention provides drug screening assays for detecting agonists or antagonists, as appropriate, of a gene (or gene product thereof) that corresponds to a selected SGE. Likewise, the identification of an SGE that can inhibit a particular pathological phenotype will indicate diagnostic assays that can assess loss-of-function or gain-of-function mutations, as appropriate, to the corresponding endogenous gene.

In general, the subject method utilizes one or more "subtractive" cell lines, and a "target" cell line. As used herein, a "desired phenotype" refers to a particular phenotype for that the user of the subject method seeks to have selectively conferred on the target cell line upon expression of an SGE. That is, the desired phenotype is dependent upon expression of an SGE, and is selectivity conferred, upon expression of the SGE, in the target cell line but not the subtractive cell line(s). The subtractive cell lines are used to remove SGEs from a variegated SGE library on the basis that these SGEs interfere with the detection of the desired phenotype in the target cells, e.g., SGEs are removed for not being selective for the target cell line with respect to conferring the desired phenotype.

Figure 1:
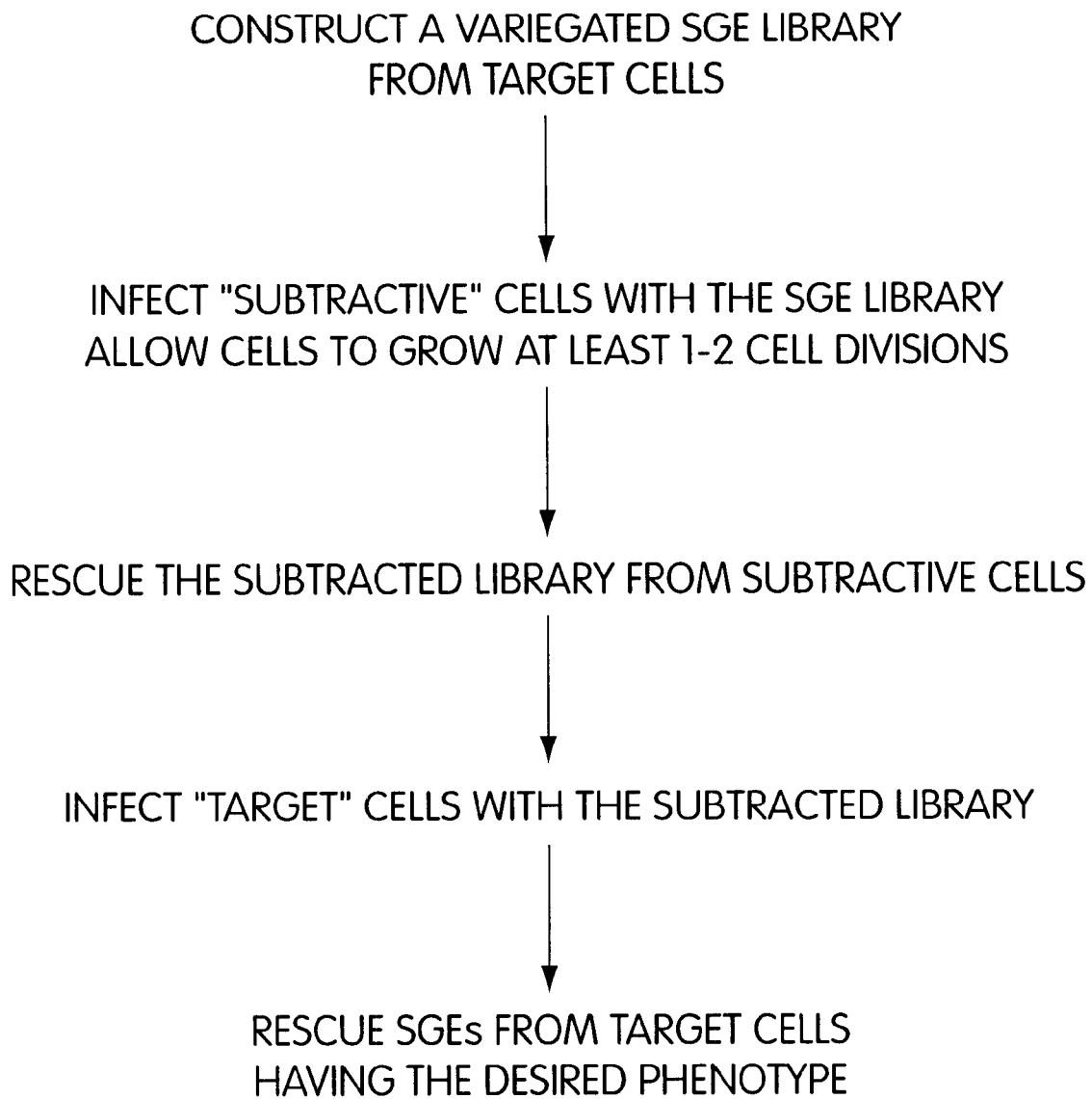
FIGS. 1–8 are flowcharts illustrating exemplary embodiments of the subject assay.

FIG. 1 illustrates a general approach of the method. The subject method can comprise a first step of providing a variegated SGE library, e.g., from the target cells. Those SGEs of the library which do not interfere with the detection of the desired phenotype in the target cells, are rescued from the subtractive cells. This sub-library, e.g., the "subtracted library", is then transfected into the target cell line. SGEs that confer the desired phenotype on the target cells can be identified, e.g., isolated and sequenced. At this point, the "subtracted SGE library" is comprised of two classes of SGE's. The first class includes DNA fragments that either do not have SGE activity (do not inhibit/interfere with gene function) or the SGE inhibits the activity of genes whose inhibition have no relevant phenotype in the screen. We expect that the majority of the library belong to this class. The second class contains functional SGEs that interfere with the function of genes whose inhibition confer the desired phenotype. We expect that a small fraction of the enriched SGE library will belong to this class. To enrich the second group of the SGEs we utilize a repeated transfection→selection→amplification cycle. The result of this cycle is that SGEs with the desired phenotype are amplified while SGEs with no relevant phenotypes are lost from the library. The transfection→selection→amplification cycle continues until substantially all of the transfected cells displays the desired phenotype. These SGEs, by virtue of the enrichment step, will selectively confer the desired phenotype on the target cell population, selectively at least with respect to the various subtractive cell lines used in the enrichment step.

For instance, in one embodiment, the present invention provides a selection method that allows fast recovery and identification of functional gene fragments that selectively inhibit growth of, e.g., are cytostatic or cytotoxic for, particular cell-types—such as transformed cells. An advantage of the subject method is that it permits phenotypic selection of lethal SGEs through dominant inactivation of genes critical to growth in one cell type but not another. For example, the subject method can be used to identify SGEs that are lethal to tumor cells, but which do not substantially interfere with the growth or viability of normal cells.

Figure 2:
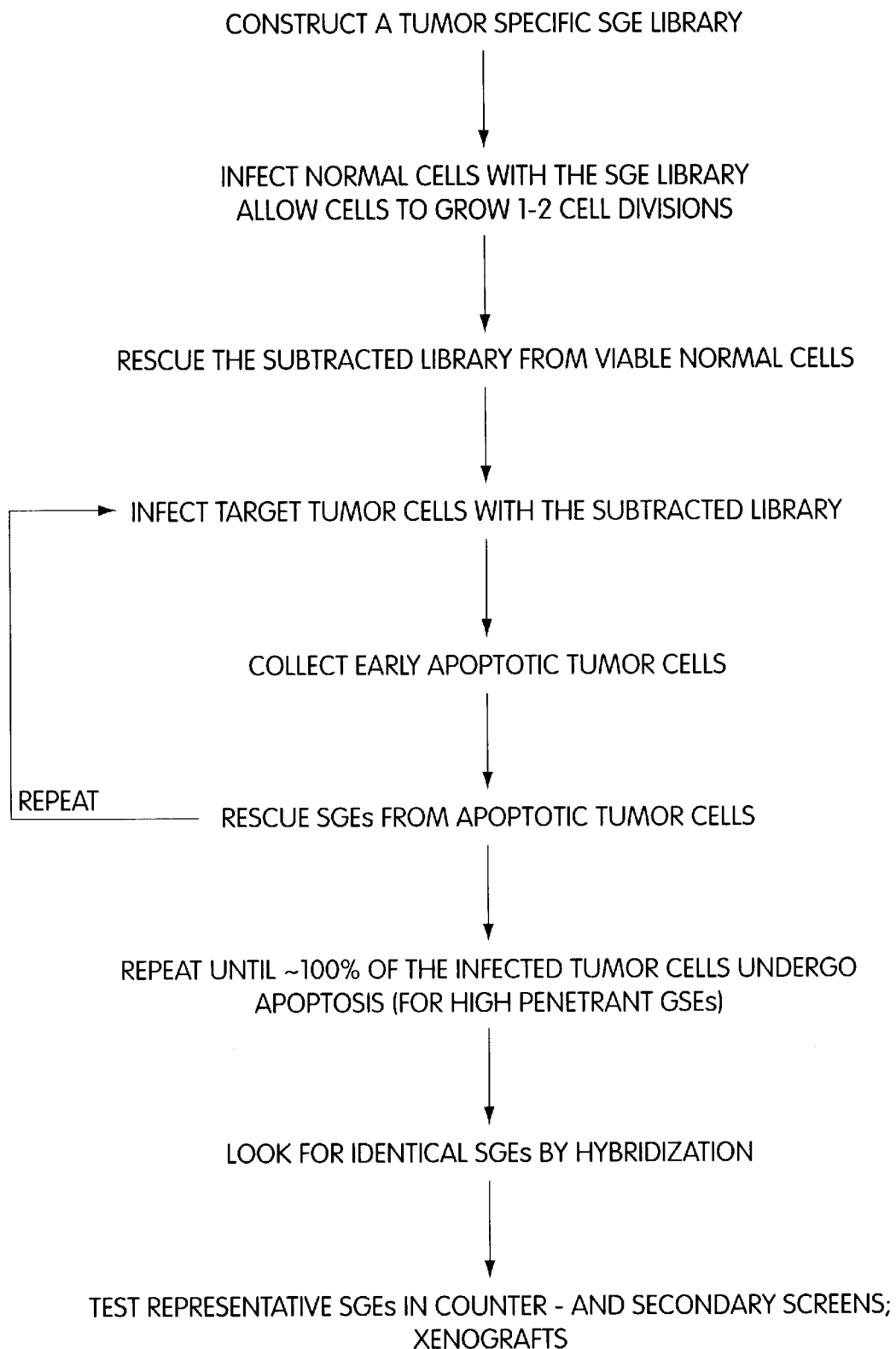

FIG. 2 illustrates an exemplary mode for performing the method of the present invention to identify SGEs that inhibit growth of transformed cells, e.g., tumor cells. An SGE library is provided in the form of a library of expression vectors, i.e., that is variegated with respect to the sequence of the SGE provided in the individual vectors of the library. In the illustrated scheme, the SGE library is generated from nucleic acid isolated from tumor cells. The SGE library is transfected into subtractive cells, e.g., such as the untransformed cell that correspond to the tumor cell from which the SGE library is generated. To illustrate, the SGE library can be generated from cDNA isolated from a basal cell carcinoma, and subtractive cells can be normal keratinocytes.

The SGE expression vectors are rescued from the those subtractive cells that are viable after several divisions under conditions wherein the SGEs are expressed. The rationale of this enrichment step is based at least in part are the understanding that a number of the SGE sequences will inhibit housekeeping genes, an event that would be cytotoxic to both normal and transformed cells. Cells that have been transfected with SGEs that are lethal to normal cells will die, and those SGE sequences will be lost from the library. The rescued portion of the library will be enriched for SGE sequences that are not lethal to the subtractive cell.

The subtracted SGE library is then transfected into the target tumor cells. Transfected tumor cells that undergo apoptosis are isolated, and the SGE expression constructs are rescued from those cells. The rescued SGE sequences represent those that are not lethal to the subtractive cells, but that are eventually lethal to the target cell. The lethal SGE sequences may be recycled through one or both of the enrichment steps, e.g., in order to further enrich for specific and highly penetrant SGEs.

In general, this approach is useful to identify SGEs, and their corresponding target genes, whose activity is essential for the survival of diseased cells and/or for the maintenance of the diseased phenotype. The inhibition of the "disease specific genes" in diseased cells results in the death of the diseased cells or the reversion of the diseased cell to the normal phenotype. In contrast, the inhibition of the same function in normal cells does not have any irreversible effect on the physiology of normal cells.

The SGEs and target genes identified by this method can be used for the selective treatment of the disease or as a means for discovery of useful drug therapies. The encoded proteins can be used in drug screening assays to identify small molecular weight drugs that inhibit the function of the target gene by interfering with the function of the encoded protein. The therapeutic window of these drugs is likely to be broad since the inhibition of the gene has no effect on normal cells but lethal to the diseased cells, as demonstrated by the selectivity of the SGEs used to identify these genes.

Figure 3:
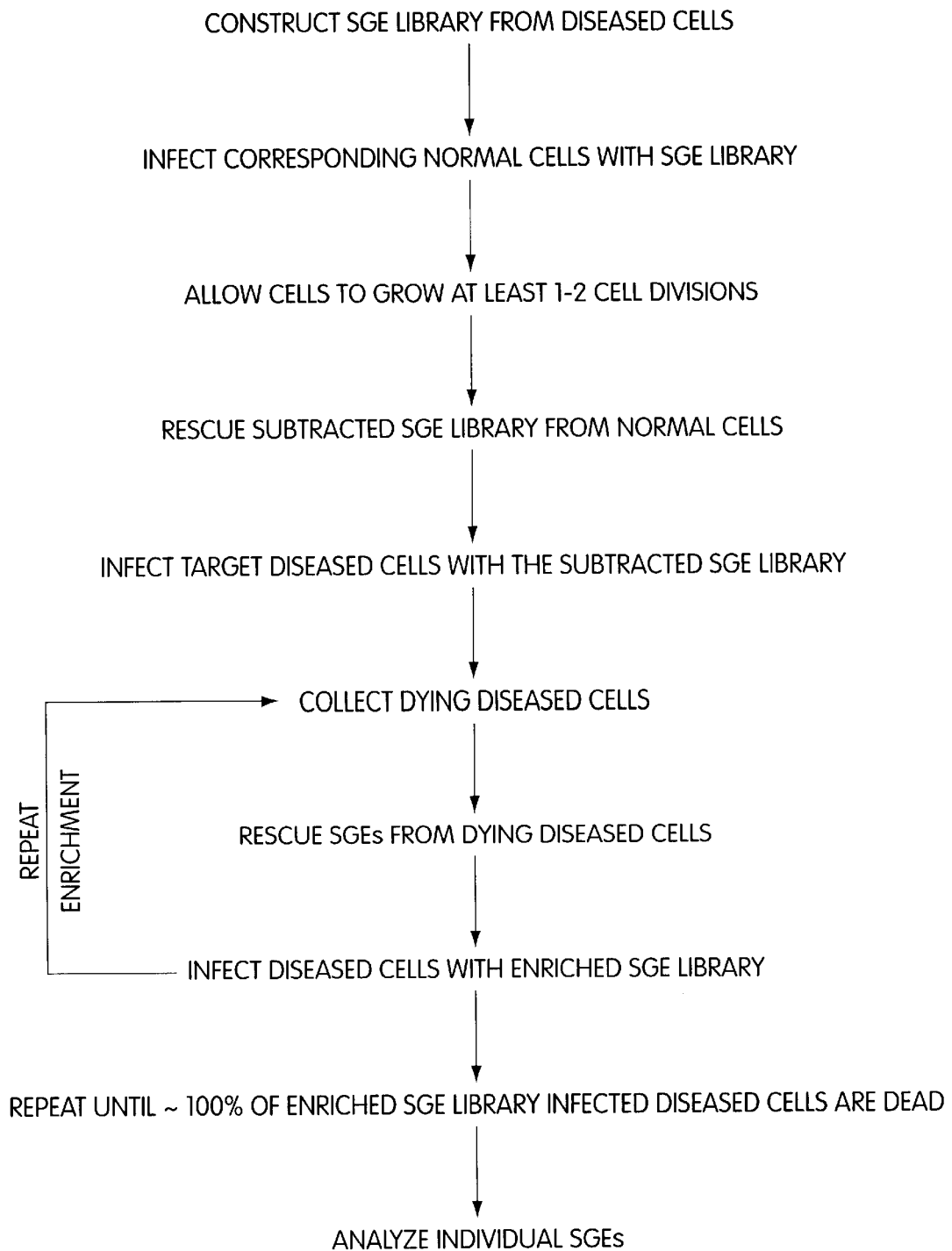

The general scheme to find "disease specific genes" is described below and illustrated in FIG. 3. The SGE library is made from diseased cells. First, the SGE library is transfected into the corresponding normal cells. After several cycles of cell division, cells that have been infected with SGEs that are lethal for the normal cells, will die and will be lost from the library. This subtracted library will be recovered from normal cells and will be used to transfect the diseased cells. SGEs will be rescued from dying diseased cells, amplified and re-transfected into the diseased cells. This cycle will be continued until substantially all of the diseased cells are dying after the transfection of the enriched SGE library. At this point, individual SGEs will be rescued and their redundancy in the enriched SGE library will be determined by hybridization. After sequencing the SGEs, their endogenous gene target will be determined. The specificity of the GSEs can further be investigated after transfection into a panel of normal and other diseased cells.

In other embodiments, the assay can be derived to identify SGEs that selectively inhibit the proliferation of virally-infected cells, e.g., but not normal cells. For example, the SGE library can be enriched for SGEs that do not inhibit proliferation or viability of normal T lymphocytes, but that are cytotoxic or cytostatic for HIV-infected T lymphocytes. Such SGEs may be useful for human therapeutic applications, such as antiviral therapy. The endogenous gene corresponding to the selectively lethal SGEs can also be, as described below, the target of a drug screening assay for identifying other agents that, by mimicking the SGE, have selective antiviral activity.

In similar fashion, the subject method can be used to identify SGEs that inhibit replication of pathogenic viruses in particular cell-types, and then to generate genetically modified cells using the SGE. Genetically modified cells according to the invention can provide benefits, such as cell-specific virus resistance, which can be commercially important in biotechnology processes using living cells, as well as in food crops derived from virus-resistant cells, or even in agriculturally important transgenic animals.

In another embodiment, improved agricultural plants can be produced from genetic modification by identification of SGEs that suppress genes responsible for undesirable properties, e.g., sensitivity to pesticides, cross-pollination of inbred plants, or other agriculturally significant trait. Thus, the SGEs can be used to create transgenic plants lacking these undesirable traits, or to develop small molecules or other agents that mimic the ability of the SGE to confer such traits (e.g., by modulating the activity of the corresponding endogenous gene or gene product).

Figure 4:
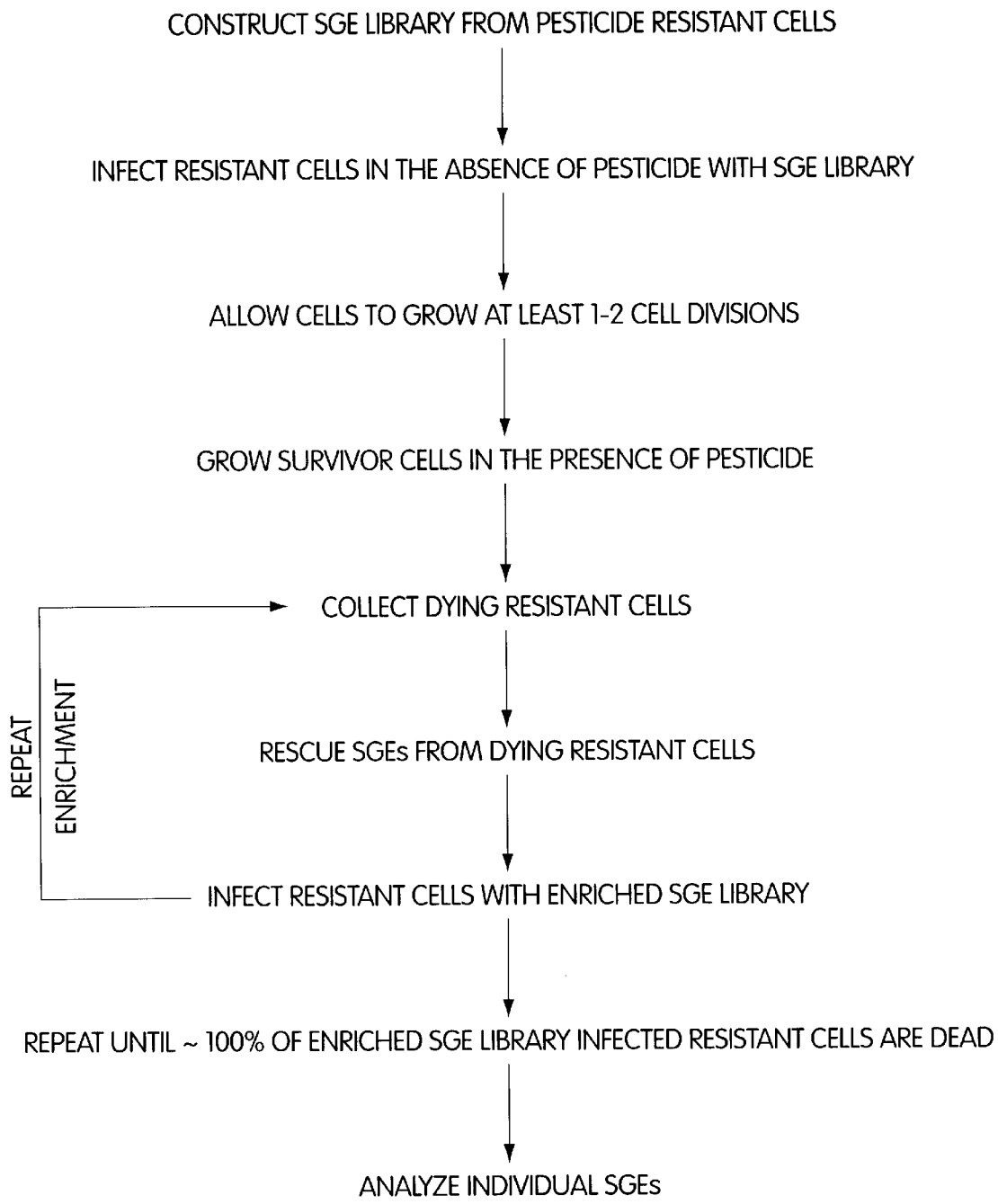

FIG. 4 illustrates a scheme to isolate SGEs which suppress genes required for pesticide resistance in plants. For this application the SGE library is made from pesticide resistant cells in a plant expression vector system. The variegated SGE library is infected into resistant cells in the absence of pesticides (subtractive cells) to eliminate normal lethal SGEs. The infected survivor cells are incubated with the pesticide (in this case no need for the rescue of the subtracted library) and death cells are collected. The SGEs are rescued, amplified, re-infected and rescued again from the death cells until ~100% of the infected cells die in the presence of the pesticide. These SGEs suppress genes whose function is required for pesticide resistance in plants.

In still other embodiments, the subject method can be used to identify SGEs, and consequently endogenous genes, which can modulate cell differentiation. For example, the enrichment step can utilize, as subtractive cells, various progenitor cells and/or conditions that give rise to certain cell-types. SGEs that do not interfere with those processes are enriched, and this sub-library is transfected into a target cell under conditions wherein the target cell would ordinarily differentiate into some more mature phenotype. SGEs that inhibit the differentiation process in the target cell (or under the target conditions), but not the subtractive cells (or subtractive conditions), can be identified by selection in this step. Thus, for example, SGEs can be identified which permit differentiation of embryonic stem cells, such as disclosed in Thomson et al. (1998) *Science* 282:1145 and Shamblott et al. (1998) *PNAS* 95:13726, to hepatocytic lineages, but which inhibit differentiation to pancreatic, lung, or other tissue derived from the primitive gut. Likewise, the subject method can be used to identify SGEs that inhibit differentiation of neural crest stem cells to a neuronal phenotype but not to epithelial or smooth muscle. As above, SGEs that effect stem cell differentiation in a selective manner indicate the identity of endogenous genes that can themselves be the target of drug screening to develop small molecule agonists or antagonist of their function.

In other embodiments, the subject method can be used to identify SGEs that inhibit a cellular response to an extracellular signal, such as a growth factor, cytokine, or other paracrine or autocrine factor. For example, TGFα is an important positive growth effector in malignant cells and plays a significant role in malignant progression. In one embodiment, the subject method first enriches for SGEs that do not inhibit growth of TGFα-responsive cells in the absence of TGFα, or enriches for SGEs that do not inhibit growth of cells which proliferate in a TGFα-independent manner. The subtracted SGE library is then transfected into TGFα-responsive cells, preferably transformed cells, in the presence of TGFα, and SGEs that inhibit growth under these conditions are identified. Similar assay formats can be used to identify SGEs that modify responsiveness of normal or transformed cells to other growth factors, cytokines, tropic factors or the like.

The subject method can also be used to identify SGEs that confer sensitivity to drugs. For example, the method can be used to generate SGEs that confer sensitivity to chemotherapeutic agents, which can lead to both diagnostic and therapeutic approaches for drug resistant cancer cells. In other embodiments, the subject method is used to identify SGEs that confer sensitivity to drugs to a pathogen, such as a drug-resistant bacteria or fungus.

Figure 5:
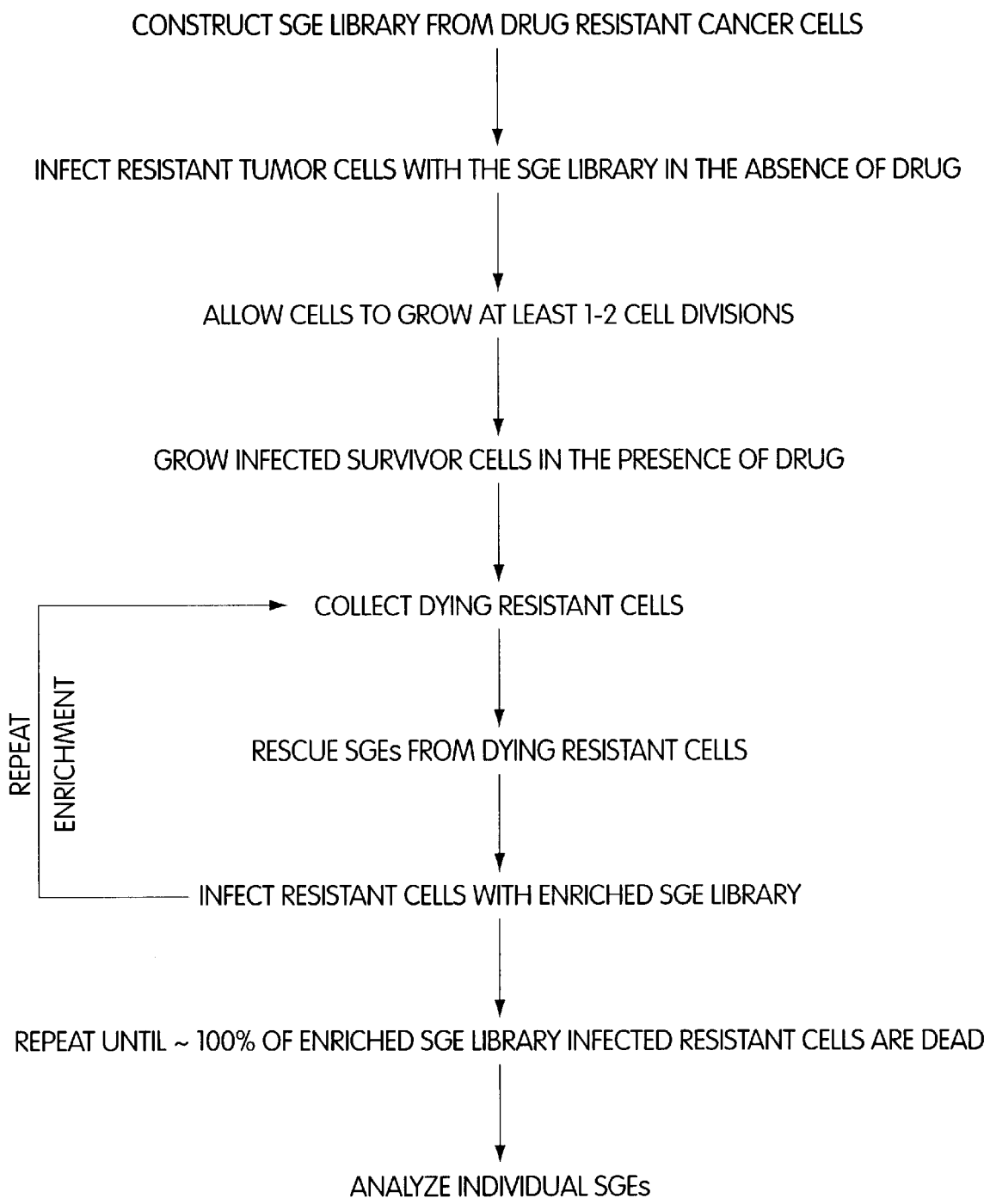

FIG. 5 depicts an approach to find SGEs which confer sensitivity to chemotherapeutic agents in cells that are normally resistant to this drug. In this example, the SGE library is constructed from drug-resistant cancer cells. The variegated SGE library is introduced into the this cells in the absence of the drug (subtractor cells) to eliminate normal lethal SGEs. Next, the survivor resistant cells are grown in the presence of the drug (target cells) and death cells are collected. The SGEs are rescued, re-infected and rescued again from death cells until ~100% of the infected cells die in the presence of the chemotherapeutic agent. These SGEs identify genes whose function is required to develop resistance against a chemotherapeutic agent.

The same approach can be applied to find SGEs that restore the sensitivity of drug-resistant microorganisms to drugs. In this example, the initial SGE library is constructed form the drug-resistant strain in an appropriate expression vector system. Than, the variegated SGE library is introduced into drug resistant cells and non-specific, normal lethal SGEs are eliminated from the library by growing the cells in the absence of the drug (subtractor cells). Next, survivor cells are grown in the presence of the drug and death cells are collected. The same steps are repeated until ~100% of the drug resistant cells transfected with the enriched SGE library die in the presence of the drug. These SGEs will confer sensitivity because they interfere with genes whose function is essential to develop resistance to the drug.

Another aspect of the present invention provides nucleic acids and/or peptides that have been identified by the subject method to selectively inhibit the growth of transformed cells, or to increase the sensitivity of transformed cells to anti-proliferative agents. Such agents may be used therapeutically or in cell culture. For example, the subject SGEs can be administered to an animal in order to inhibit growth of transformed cells, or to augment the effectiveness of a conjointly administered antiproliferative agent.

In certain embodiments, where the identified SGE encodes a peptide or protein, the coding sequence for the SGE is used to generate an expression constructs. In other embodiments, where the peptide is sufficiently short, the peptide can converted to a peptidomimetic. In still other embodiments, where the SGE is a nucleic acid that functions as an antisense molecule or decoy, the SGE can be provided in an expression construct that is transcribed to RNA corresponding to the SGE. Alternatively, SGEs that are inhibitory as nucleic acids can be provided as non-hydrolyzable analogs.

Still another aspect of the present invention provides a drug screening assay for identifying agents that inhibit or potentiate (as appropriate) the activity of an endogenous gene product identified as the source of a selective SGE identified by the present method. The invention also provides preparations of such compounds, and methods for their use in such applications as cell culture additives, pharmaceutical preparations, feedstock supplements, and agricultural formulations.

ii. Definitions

For convenience, certain terms employed in the specification, examples, and appended claims are collected here.

As used herein, the term "vector" refers to a nucleic acid molecule capable of transporting another nucleic acid to that it has been linked. One type of vector is a genomic integrated vector, or "integrated vector", which can become integrated into the chromosomal DNA of the host cell. Another type of vector is an episomal vector, i.e., a nucleic acid capable of extra-chromosomal replication. Vectors capable of directing the expression of genes to that they are operatively linked are referred to herein as "expression vectors". In the present specification, "plasmid" and "vector" are used interchangeably unless otherwise clear from the context.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides.

As used herein, the term "gene" or "recombinant gene" refers to a nucleic acid comprising an open reading frame encoding a polypeptide of the present invention, including both exon and (optionally) intron sequences. A "recombinant gene" refers to nucleic acid encoding such regulatory polypeptides, that may optionally include intron sequences that are derived from chromosomal DNA. The term "intron" refers to a DNA sequence present in a given gene that is not translated into protein and is generally found between exons. As used herein, the term "transfection" means the introduction of a nucleic acid, e.g., an expression vector, into a recipient cell by nucleic acid-mediated gene transfer.

A "protein coding sequence" or a sequence that "encodes" a particular polypeptide or peptide, is a nucleic acid sequence that is transcribed (in the case of DNA) and is translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from procaryotic or eukaryotic mRNA, genomic DNA sequences from procaryotic or eukaryotic DNA, and even synthetic DNA sequences. A transcription termination sequence will usually be located 3' to the coding sequence.

However, as described below, the generic term "coding sequence" may refer to, as the context permits, sequences that are transcribed to produce RNA that is itself directly active (as a potential SGE), as opposed to a polypeptide translated therefrom.

Likewise, "encodes", unless evident from its context, will be meant to include DNA sequences that encode a polypeptide, as the term is typically used, as well as DNA sequences that are transcribed into inhibitory antisense molecules.

An "initial SGE library" is a library of coding sequences for potential synthetic genetic elements.

A "subtracted SGE library" is the sub-library of the original SGE library that was generated by the infection of the library into subtractor cells to remove SGE's whose activity would interfere with the screening of the SGE library in the target cells.

An "enriched SGE library" is a collection of SGE's that confers the desired phenotype in target cells. The enriched library is generated by repeated transfection→selection→amplification of the subtracted library in target cells.

"Subtractive cells" are those cells that are used to remove those SGEs from a variegated SGE library that confer a non-desirable phenotype.

"Target cells" are cells are used to identify SGEs from an SGE library that confer the desired phenotype on the target cells.

A "normal lethal SGE" is a synthetic genetic element that is lethal to one or more subtractive cell-types.

A "selective lethal SGE" is a synthetic genetic element that is lethal to a target cell-types, but not to a subtractive cell-type.

The term "loss-of-function", as it refers to SGEs, refers to those SGEs that inhibit expression of a gene, or render the gene product thereof to have substantially reduced activity, or preferably no activity relative to one or more functions of the corresponding wild-type gene product.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence. On the other hand, "expression" of an antisense sequence or ribozyme will be understood to refer to the transcription of the recombinant gene sequence as it is the RNA product that is directly active.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

By "recombinant virus" is meant a virus that has been genetically altered, e.g., by the addition or insertion of a heterologous nucleic acid construct into the particle.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, where anti-sense expression occurs from the transferred gene, the expression of a naturally-occurring form of a protein is disrupted.

"Transient transfection" refers to cases where exogenous DNA does not integrate into the genome of a transfected cell, e.g., where episomal DNA is transcribed into mRNA and translated into protein.

A cell has been "stably transfected" with a nucleic acid construct when the nucleic acid construct is capable of being inherited by daughter cells.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences can be directly or indirectly regulated by the target receptor protein. Exemplary transcriptional control sequences are promoter sequences. A reporter gene is meant to include a promoter-reporter gene construct that is heterologously expressed in a cell.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

As used herein, "proliferating" and "proliferation" refer to cells undergoing mitosis.

As used herein, "immortalized cells" refers to cells that have been altered via chemical, genetic, and/or recombinant means such that the cells have the ability to grow through an indefinite number of divisions in culture.

The "growth state" of a cell refers to the rate of proliferation of the cell and the state of differentiation of the cell.

iii. Exemplary Embodiments of Isolation Method

The SGEs identified by the present method may function to inhibit the function of an endogenous gene at the level of nucleic acids, e.g., by an antisense or decoy mechanism, or by encoding a polypeptide that is inhibitory through a mechanism of interference at the protein level, e.g., a dominant negative fragment of the native protein. On the other hand, certain SGEs may function to potentiate (including mimicking) the function of an endogenous gene by encoding a polypeptide which retains at least a portion of the bioactivity of the corresponding endogenous gene, and may in particular instances be constitutively active.

In one embodiment, the initial SGE library is generated from total cDNA, that may be further fragmented, and provided in the form of an expression library. Preferably, the inserts in the library will range from about 100 bp to about 700 bp and more preferably, from about 200 bp to about 500 bp in size.

For cDNA-derived libraries, the nucleic acid library can be a normalized library containing roughly equal numbers of clones corresponding to each gene expressed in the cell type from which it was made, without regard for the level of expression of any gene.

The initial SGE libraries can be generated to include both sense and antisense coding (and non-coding sequences) sequences. Transcription of the SGE sequence in the subtractive and target cells will create antisense RNA that may inhibit transcription of the corresponding endogenous gene. Translation of appropriate protein coding sequences in the transcribed RNA can produce full-length and truncated forms of endogenous proteins, as well as short peptides, the differential biological effects of that are assessed in the subtractive and target cells.

U.S. Pat. No. 5,702,898 describes a method to normalize a cDNA library constructed in a vector capable of being converted to single-stranded circles and capable of producing complementary nucleic acid molecules to the single-stranded circles comprising: (a) converting the cDNA library in single-stranded circles; (b) generating complementary nucleic acid molecules to the single-stranded circles; (c) hybridizing the single-stranded circles converted in step (a) with complementary nucleic acid molecules of step (b) to produce partial duplexes to an appropriate Cot; (e) separating the unhybridized single-stranded circles from the hybridized single-stranded circles, thereby generating a normalized cDNA library.

In certain embodiments, the initial SGE library can be a subtractive cDNA library. Many strategies have been used to create subtractive libraries, and can be readily adapted for use in the present method. One approach is based on the use of directionally cloned cDNA libraries as starting material (Palazzolo and Meyerowitz, (1987) Gene 52:197; Palazzolo et al. (1989) Neuron 3:527; Palazzolo et al. (1990) Gene 88:25). In this approach, cDNAs prepared from a first source tissue or cell line are directionally inserted immediately downstream of a bacteriophage T7 promoter in the vector. Total library DNA is prepared and transcribed in vitro with T7 RNA polymerase to produce large amounts of RNA that correspond to the original mRNA from the first source tissue. Sequences present in both the source tissue and another tissue or cells, such as normal tissue, are subtracted as follows. The in vitro transcribed RNA prepared from the first source is allowed to hybridize with cDNA prepared from either native mRNA or library RNA from the second source tissue. The complementarity of the cDNA to the RNA makes it possible to remove common sequences as they anneal to each other, allowing the subsequent isolation of unhybridized, presumably tissue-specific, cDNA. This approach is only possible using directional cDNA libraries, since any cDNA sequence in a non-directional library is as likely to be in the "sense" orientation as the "antisense" direction (sense and antisense are complementary to each other). A cDNA sequence unique to a tissue would be completely removed during the hybridization procedure if both sense and antisense copies were present.

In one directional cloning strategy, which can be used to generate an initial SGE library, a DNA sequence encoding a specific restriction endonuclease recognition site (usually 6–10 bases) is provided at the 5' end of an oligo(dT) primer. This relatively short recognition sequence does not affect the annealing of the 12–20 base oligo(dT) primer to the mRNA, so the cDNA second strand synthesized from the first strand template includes the new recognition site added to the original 3' end of the coding sequence. After second strand cDNA synthesis, a blunt ended linker molecule containing a second restriction site (or a partially double stranded linker adapter containing a protruding end compatible with a second restriction site) is ligated to both ends of the cDNA. The site encoded by the linker is now on both ends of the cDNA molecule, but only the 3' end of the cDNA has the site introduced by the modified primer. Following the linker ligation step, the product is digested with both restriction enzymes (or, if a partially double stranded linker adapter was ligated onto the cDNA, with only the enzyme that recognizes the modified primer sequence). A population of cDNA molecules results which all have one defined sequence on their 5' end and a different defined sequence on their 3' end.

A related directional cloning strategy developed by Meissner et al. (1987) *PNAS* 84:4171), requires no sequence-specific modified primer. Meissner et al. describe a double stranded palindromic BamHI/HindIII directional linker having the sequence d(GCTTGGATCCAAGC), that is ligated to a population of oligo(dT)-primed cDNAs, followed by digestion of the ligation products with BamHI and HindIII. This palindromic linker, when annealed to double stranded form, includes an internal BamHI site (GGATCC) flanked by 4 of the 6 bases that define a HindIII site (AAGCTT). The missing bases needed to complete a HindIII site are d(AA) on the 5' end or d(TT) on the 3' end. Regardless of the sequence to which this directional linker ligates, the internal BamHI site will be present. However, HindIII can only cut the linker if it ligates next to an d(AA):d(TT) dinucleotide base pair. In an oligo(dT)-primed strategy, a HindIII site is always generated at the 3' end of the cDNA after ligation to this directional linker. For cDNAs having the sequence d(TT) at their 5' ends (statistically 1 in 16 molecules), linker addition will also yield a HindIII site at the 5' end. However, because the 5' ends of cDNA are heterogeneous due to the lack of processivity of reverse transcriptases, cDNA products from every gene segment will be represented in the library.

In other embodiments, the SGE library is generated from genomic DNA fragments. Preferably, the inserts in the library will range from about 100 bp to about 700 bp and more preferably, from about 200 bp to about 500 bp in size. Such SGE libraries, in addition to encoding polypeptide and antisense molecules that may be functional SGEs in the test method, may also "encode" decoy molecules, e.g., nucleic acid sequences which correspond to regulatory elements of a gene and which can inhibit expression of the gene by sequestering, e.g., transcriptional factors, and thereby competing for the necessary components to express the endogenous gene.

In yet another embodiment, the SGE library is generated by randomly fragmenting a single gene to obtain a random fragment expression library derived exclusively from the gene of interest. As a practical matter, such a library will contain a much greater variety of SGEs derived from the gene of interest than will a random fragment library prepared from total cDNA. Consequently, the likelihood of obtaining optimized SGEs, that have a differential activity according to the present method, from the single gene random fragment library is much higher.

In one embodiment, purified DNA corresponding to the gene or genome to be suppressed is first randomly fragmented by enzymatic, chemical, or physical procedures. In a preferred embodiment, random fragments of DNA are produced by treating the DNA with a nuclease, such as DNase I. The random DNA fragments are incorporated as inserts in a SGE library. For general principles of DNase I partial digestion and library construction see Molecular Cloning, A Laboratory Manual, Sambrook et al., Eds., Cold Spring Harbor Laboratory, Cold Spring Harbor, N.Y. (1989). In certain embodiments the inserted fragment may be expressed as part of a fusion protein. In other embodiments the inserted fragment alone may be expressed. In another embodiment, ribozyme-encoding sequences may be inserted directly adjacent to the insert to allow for selection of most efficient ribozyme-antisense clones. In still other embodiments the gene suppression element library may be further modified by random mutagenesis procedures known in the art. The inserted fragments may be expressed from either a constitutive or an inducible promoter.

In still another embodiment, the subject method is carried out with a SGE library encoding a variegated population of small peptides, e.g., 4–25 amino acid residues in length. The library can be generated from coding sequences of total cDNA, or single genes, or can be random or semi-random in sequence. Small peptide fragments, corresponding to only a minute portion of a protein, can inhibit the function of that protein in vivo.

There are a wide range of expression constructs which can be used to express the subject SGEs in the present method. In preferred embodiments, the SGE library is provided in a vector which can be transfected, and the library expressed, in both the target and subtractive cells. Moreover, it will generally be desirable that the vector be recoverable from the cells.

The SGEs can be recombinantly expressed using, e.g., expression vectors containing the SGE coding sequence operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of the SGE sequence in the subtractive and target cells. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences may be used in the subject expression vectors, such as a viral LTR (e.g., the LTR of the Moloney murine leukemia virus), the early and late promoters of SV40, adenovirus or cytomegalovirus (CMV) immediate early promoter, the promoter for 3-phosphoglycerate kinase or other glycolytic enzymes, the promoters of acid phosphatase, e.g., Pho5, the promoters of the yeast cc-mating factors, the polyhedron promoter of the baculovirus system and other sequences known to control the expression of genes in prokaryotic or eukaryotic cells or their viruses, and various combinations thereof. It should be understood that the design of the expression vector may depend on such factors as the choice of the host cell to be transfected and/or the type of protein desired to be expressed. Moreover, the vector's copy number, the ability to control that copy number and the expression of any other proteins encoded by the vector, such as antibiotic markers, should also be considered.

Approaches to expressing the SGE library in subtractive and target cells include insertion of the SGE coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin), polylysine conjugates, gramacidin S, artificial viral envelopes or other such intracellular carriers, as well as direct injection of the gene construct or calcium phosphate precipitation carried out in vivo. It will be appreciated that because the efficiency of transduction of the target and subtractive cells can represent a critical step in sampling the SGE library, choice of the particular transfection system will depend on such factors as the phenotype of the intended target.

A preferred approach for introduction of the SGE library into a subtractive or target cell is by use of a viral vector. Infection of cells with a viral vector has the advantage that a large proportion of the targeted cells can receive the nucleic acid. Additionally, the SGE coding sequences contained in the viral vector can be expressed efficiently in cells that have taken up viral vector nucleic acid.

Retrovirus vectors are a preferred recombinant delivery system for the transfer of the SGE constructs into mammalian cells, particularly into humans. These vectors provide efficient delivery of genes into cells, and the transferred nucleic acids are stably integrated into the chromosomal DNA of the host.

In preferred uses of retroviruses, e.g., to ensure the safety of their use, the vectors will used in conjunction with specialized cell lines (termed "packaging cells") which produce only replication-defective retroviruses (for a review see Miller, A. D. (1990) *Blood* 76:271). Thus, recombinant retrovirus can be constructed in which part of the retroviral coding sequence (gag, pol, env) has been replaced. The replication defective retrovirus is then packaged into virions which can be used to infect a target cell through the use of a helper virus by standard techniques. Protocols for producing recombinant retroviruses and for infecting cells in vitro with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM that are well known to those skilled in the art. Examples of suitable packaging virus lines for preparing both ecotropic and amphotropic retroviral systems include Crip, Cre, 2 and Am. Retroviruses have been used to introduce a variety of genes into many different cell types in vitro (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad Sci. USA* 88:8039–8043; Ferry et al. (1991) *Proc. Natl. Acad Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

In certain preferred embodiments, the SGE library is cloned into a retroviral expression vector to create a variegated vector library. Exemplary vectors for use in the present method are described in, for example, U.S. Pat. No. 5,753,432, 5,665,550, 5,206,352, and PCT publications WO 98/12339.

The SGE library is used to transfect the subtractive cells, e.g., by introducing the library into the cells by procedures appropriate to the vector chosen and well known in the art. See, e.g., Keown et al., *Methods Enzymol.* 185:527–536 (1990). The genetically modified subtractive cells containing SGEs can be screened for or selected in a variety of ways.

The transfected subtractive cells are cultured for a period of time sufficient for the cells to at least develop the desired phenotype, or one which interferes with its detect, in order to permits selection of cells expressing SGEs which do not exhibit such phenotypes.

For example, where the desired phenotype is lethality, cells that are viable after expression of the SGE library can be amplified in the culture and isolated after a sufficient number of passages for the normal lethal SGEs to kill their host cells. The viable cells can be isolated from the culture supernatant, e.g., by centrifugation, and the SGE vectors isolated from the intact cells. However, it may be desirable to separate the cells before death and lysis of the cells expressing lethal SGEs occurs. In such embodiments, cells can be differentially sorted, e.g., by fluorescence activated cell sorters (FACs), affinity purification techniques or other well known markers. For example, the ability of viable cells to incorporate BrdU can provide for a FACs-selectable marker.

Continuing with the illustrative example of selective lethality, in certain embodiments it may be necessary to stimulate the subtractive cells with a mitogen(s), or by repassage in order to cause proliferation. In addition to providing a proliferative signal against which the anti-proliferative abilities of the SGE library are selected, such stimulation can give rise to changes in cell markers, such as cell surface proteins, which can be detected by FACs, or changes in expressions of a reporter gene.

In certain embodiments, a heterologous reporter gene construct can be used to provide the function of an indicator gene. Reporter gene constructs are prepared by operatively linking a reporter gene with at least one transcriptional regulatory element which is, e.g., activated by mitogenic signals. Many reporter genes and transcriptional regulatory elements are known to those of skill in the art and others may be identified or synthesized by methods known to those of skill in the art.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (dewet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368); β-lactamase or GST.

Transcriptional control elements for use in the reporter gene constructs, or for modifying the genomic locus of an indicator gene include, but are not limited to, promoters, enhancers, and repressor and activator binding sites. Again, using the selective lethality embodiments to illustrate, suitable transcriptional regulatory elements may be derived from the transcriptional regulatory regions of genes whose expression is rapidly induced, generally within minutes, of contacting the cell with a mitogenic agent. Examples of such genes include, but are not limited to, the immediate early genes (see, Sheng et al. (1990) Neuron 4: 477–485), such as c-fos. Immediate early genes are genes that are rapidly induced upon mitogenic stimulation. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of mitogenic simulation, induction that is transient and independent of new protein synthesis, subsequent shut-off of transcription requires new protein synthesis, mRNAs transcribed from these genes have a short half-life, and lack of expression in apoptotic cells. It is not necessary for all of these properties to be present.

Other promoters and transcriptional control elements, in addition to those described above, include the vasoactive intestinal peptide (VIP) gene promoter (cAMP responsive; Fink et al. (1988), Proc. Natl. Acad. Sci. 85:6662–6666); the somatostatin gene promoter (cAMP responsive; Montminy et al. (1986), Proc. Natl. Acad. Sci. 8.3:6682–6686); the proenkephalin promoter (responsive to cAMP, nicotinic agonists, and phorbol esters; Comb et al. (1986), Nature 323:353–356); the phosphoenolpyruvate carboxy-kinase gene promoter (cAMP responsive; Short et al. (1986), J. Biol. Chem. 261:9721–9726); the NGFI-A gene promoter (responsive to NGF, cAMP, and serum; Changelian et al. (1989). Proc. Natl. Acad. Sci. 86:377–381); and others that may be known to or prepared by those of skill in the art.

In the case of receptors which modulate cyclic AMP, for example, a transcriptional-based readout can be constructed using the cyclic AMP response element binding protein, CREB, that is a transcription factor whose activity is regulated by phosphorylation at a particular serine (S133). When this serine residue is phosphorylated, CREB binds to a recognition sequence known as a CRE (cAMP Responsive Element) found to the 5' of promoters known to be responsive to elevated cAMP levels. Upon binding of phosphorylated CREB to a CRE, transcription from this promoter is increased.

Therefore, a transcriptional-based readout can be constructed in cells containing a reporter gene whose expression is driven by a basal promoter containing one or more CRE. Changes in the intracellular concentration of $Ca^{++}$ (e.g., a result of alterations in the activity of the growth factor receptor upon engagement with a growth factor) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, mitogenic stimulation of the cell may result in phosphorylation of CREB and increased transcription from the CRE-construct, while inhibition of PLC activity may result in decreased transcription from the CRE-responsive construct.

In the exemplary embodiments of the subject method for score for SGEs which selectively inhibit or potentiate growth factor, reporter gene readouts as described above can be employed, as can direct detection of second messenger formation.

Whatever the ultimate method, subtractive cells which do not develop the desired phenotype upon expression of an SGE are isolated, and the SGE sub-library representative of those cells is isolated by standard protocols. The isolated vectors are then transfected into the target cells—those cells for which selective SGEs are desired.

As above, the target cells are cultured for a time sufficient for the desired phenotype to develop as a detectable signal. For instance, in one of the selective lethal embodiments, where cell lysis occurs due to apoptosis, those vectors encoding lethal SGEs can be isolated from the cell debris, e.g., from the culture supernatant. However, a more pragmatic approach is to identify the lethal phenotype before the cells lyse, and isolate the SGE vectors from a relatively intact, albeit dying, cell.

Thus, in one embodiment, cells expressing lethal SGEs are isolated on the basis of expression of an early marker for apoptosis. To illustrate, the apoptotic activity of the SGE library can be detected using a commercially available kit, Apoptosis Detection Kit, from R & D SYSTEMS (Minnesota) in which annexin V, a member of the calcium and phospholipid binding proteins, is used to detect apoptosis, e.g., following the protocol recommended by the manufacturer. Fluorescein-labeled annexin V and propidium iodide are added to the cells. The cells expressing phosphatidylserine on the outer leaflet of cell membranes bind annexin V, and cells with a compromised cell membrane allow propidium iodide to bind to the cellular DNA. The resulting cells, when immediately analyzed by flow cytometry, can present three potential populations of cells: live cells which will not stain with either fluorochrome, necrotic cells which will stain with both fluorochrome, and cells undergoing apoptosis which will stain only with the annexin V-FITC reagent. Analysis, and cell separation, can be performed on cytometers equipped with a single laser emitting excitation light at 488 nm. Thus, SGEs which selectively induce apoptosis can be distinguished from those which cause necrotic cell death.

Another potential approach to isolate cells expressing lethal SGEs is to collect "floating" cells and rescue the SGEs from those cells.

Alternatively, the cells can be loaded with small, cell permeable, fluorogenic caspase substrates. The activation of apoptotic caspases can be detected in vivo by the cleavage of the substrate that increases fluorescence. Fluorescent cells can be identified and separated by FACS (Packard B Z et al., Proc. Natl. Acad. Sci., 93:11640–11645, 1996).

In the subject method, SGEs are finally obtained from the selected subtractive or target cells by procedures known in the art. In one embodiment, the SGE is isolated by use of the polymerase chain reaction with DNA obtained from the selected cells and with primers homologous to sites on the vector flanking the insert. In another embodiment, the SGE expression library may be prepared in shuttle vectors, allowing efficient recovery of shuttle vectors containing SGEs. Finally, SGEs can be isolated by standard cloning techniques well known in the art using vector specific probes although this might be more laborious than other embodiments herein described.

After identification in the target cell phase of the method, the isolated SGE inserts of the expression library may be sequenced. Alternatively, and preferably, the rescued library clone may be further tested for its ability to selectively confer the desired phenotype in other selection assays, prior to nucleotide sequence determination. Determination of the nucleotide sequence, of course, results in the identification of the SGE.

A. Selective Killing of HIV Infected CD4+ T Lymphocytes:

Following the first burst of viral replication that immediately follows HIV-1 infection, there is a relatively long period of clinical latency (8 to 12 years). During this time the viral load is relatively stable which reflect to a relatively constant rate of new infection and death of the infected cells. The virus infected CD4+ cells display impaired T-cell functions (i.e., colony formation, expression of IL-2 receptor, etc.), antigen-specific responses, mitogen/antigen induced cell proliferation or signal transduction. The cellular changes are caused by the expressed viral regulatory proteins such as nef, tat, vpu, env, serve the better adaptation of the infected cells to the needs of the virus. Since the physiology of the HIV-1 infected CD4+ T lymphocytes is different from the physiology of the normal cells these differences can be utilized to identify genes whose function is essential for the survival of the virus infected cells but not essential for the survival of normal cells.

For this application the SGE library is made from HIV-1 infected CD4+ T lymphocytes. The library is transfected into the subtractor, normal CD4+ T lymphocytes and the transfected cells are allowed to undergo at least two rounds of cells division. This step leads to the subtraction of the "normal lethal SGEs" from the library. Living cells are separated from death cells on a Percoll gradient. SGEs are rescued from the living cells and used to transfect the target cells, HIV-1 infected CD4+ T lymphocytes. SGE's are rescued from early apoptotic cells that have been isolated by one of the methods described above. This enriched SGE library is used to repeat the selection cycle. The selection cycles are continued until ~100% of the transfected cell undergo apoptosis. At this point individual SGE's are isolated and used to verify the selective phenotype in normal and HIV-1 infected CD4+ T lymphocytes. The selectivity of the SGE is further tested on a panel of normal cells. The ideal SGE inhibits a cellular gene whose function is not essential in any of the normal cell lines. Small molecular weight inhibitors of this gene would selectively kill HIV-1 infected CD4+cells by targeting a cellular and not a viral target.

Figure 6:
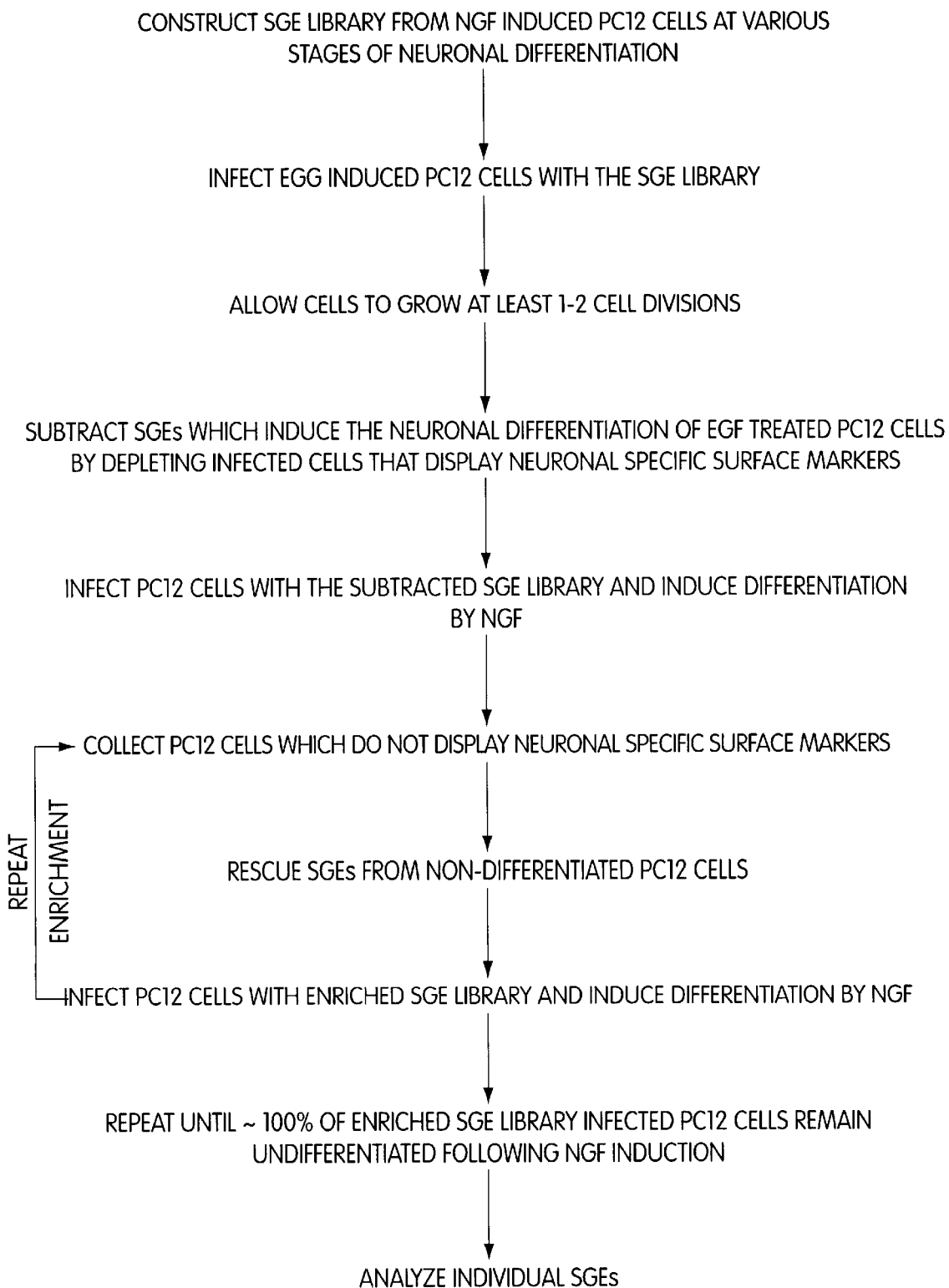

B. Regulation of Cell Differentiation:

Rat PC12 pheochromocytoma (teratocarcinoma) cells are widely used to study cell differentiation. In the presence of EGF (epidermal growth factor) these cells proliferate but the addition of NGF (nerve growth factor) induces their neuronal differentiation and they become neurons. To isolate SGEs which interfere with the NGF induced neuronal differentiation of PC 12 cells, the variagated SGE library is made from NGF treated PC12 cells at various stages of neuronal differentiation. This SGE library is introduced into PC12 cell proliferating in the presence of EGF (subtractor cell). The infected cells are allowed to undergo at least two rounds of cell division. This step leads to the subtraction of "normal lethal SGEs" from the SGE library. SGEs that might cause the differentiation of PC12 cells into neurons in the presence of EGF would also be depleted from the library using FACS or magnetic beads as well as antibodies against neuronal cell specific surface markers such as voltage-gated $Na^+$, $K^+$, $Ca^{2+}$ channels, or glutamate receptor or other neurotransmitter receptors. At this point, the subtracted SGE library is rescued from the depleted cells that do not display any neuronal cell specific phenotype and is introduced into PC12 cells. The differentiation of the subtracted SGE library transformed Pc12 cells is induced by NGF. Cells displaying neuronal cell specific surface markers are depleted and SGEs are rescued from cells that do not display any neuronal phenotype. This enriched library is reintroduced into PC12 cells and the infected cells are induced to differentiate into neurons. Again, SGEs are rescued from cells that do not display any neuronal specific phenotype. The cycle of reinfection, selection and SGE rescue is repeated until the NGF induced differentiation of 100% of the transfected PC12 cells is inhibited (FIG. 6).

Figure 7:
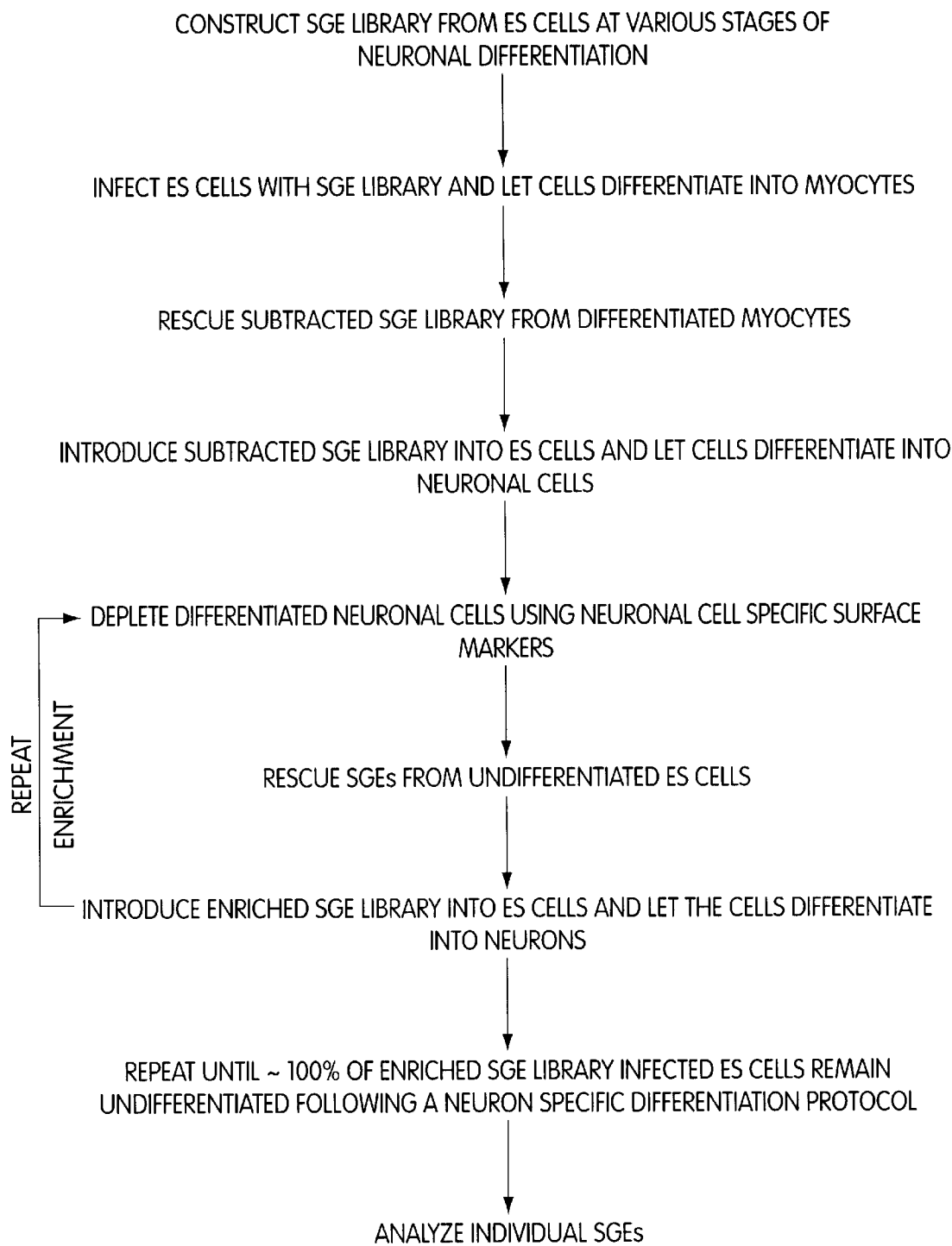

FIG. 7 illustrates another example to isolate SGEs which interfere with the neuronal differentiation of embryonic stem (ES) cells. Mouse ES cells can be induced to differentiate into neuronal and muscle cells. The differentiated neuronal cells display neuronal cell specific markers (see above) when ES cells are cultured in aggregates (embryoid bodies) and exposed to retinoic acid. To induce the neuronal differentiation of these cells, rapidly growing undifferentiated ES cells are gently trypsinized. The cell suspension is incubated for two days during which the floating aggregates are formed. The aggregates are incubated for two additional days and than fresh media is added with $5 \times 10^{-7}$ M all-trans-retinoic acid (RA). The aggregates are incubated for four days in the presence of RA (fresh media is added after two days). By the end of this eight days incubation period neuronal cells are formed and single cell suspension can be generated by trypsinization for further analysis.

To induce the differentiation of ES cells into myocytes and ultimately myotubes, ES cells are cultivated in hanging drops (800 cells/20ul) for two days. The developed embryoid bodies are cultivated in suspension for another three days, at which point single embryoid bodies are transfered to 24-well tissue culture plates to promote attachment. Differentiated myocytes can be isolated five days later by trypsinization.

The SGE library is constructed from differentiated neuronal cells to isolate SGEs which inhibit the differentiation of ES cells into neurons. Than the variegated SGE library will be introduced into ES cells and the infected cells are differentiated into myocytes (subtractor cells). Than, differentiated myocytes are collected and the subtracted SGE library will be rescued. The subtracted SGE library is introduced again into ES cells and neuronal differentiation is induced. Differentiated neuronal cells are depleted using antibodies again neuronal cell specific surface markers and SGEs are rescued from the undifferentiated cells. This enriched SGE library will be introduced into ES cells again and the infected cells are induced to differentiate into neurons. SGEs will be rescued from undifferentiated cells and reintroduced into fresh ES cells. This cycle is repeated until ~100% of the transfected ES cells which are induced to differentiate into neurons remain undifferentiated. These SGEs interfere with the function of genes whose activity plays an essential role in the neuronal differentiation of ES cells.

C. Selective Killing of Prion Infected Neuronal Cells:

Prions are infectious agents widely implicated in a variety of mammalian neurodegenerative diseases generally referred to as transmissible spongiform encephalopathies (for example Creutzfeldt-Jacob disease). In the brain of the infected patients there is plaque formation, the deposition of birefringent rods and fibrillar structures that destroy the host neurons and ultimately leads to death. The infectivity of prions is primarily associated with an aberrant conformation of a host protein, the prion protein, induced by the prion itself. The cellular prion protein is encoded by the cellular PrP gene and its normal function is unknown.

Figure 8:
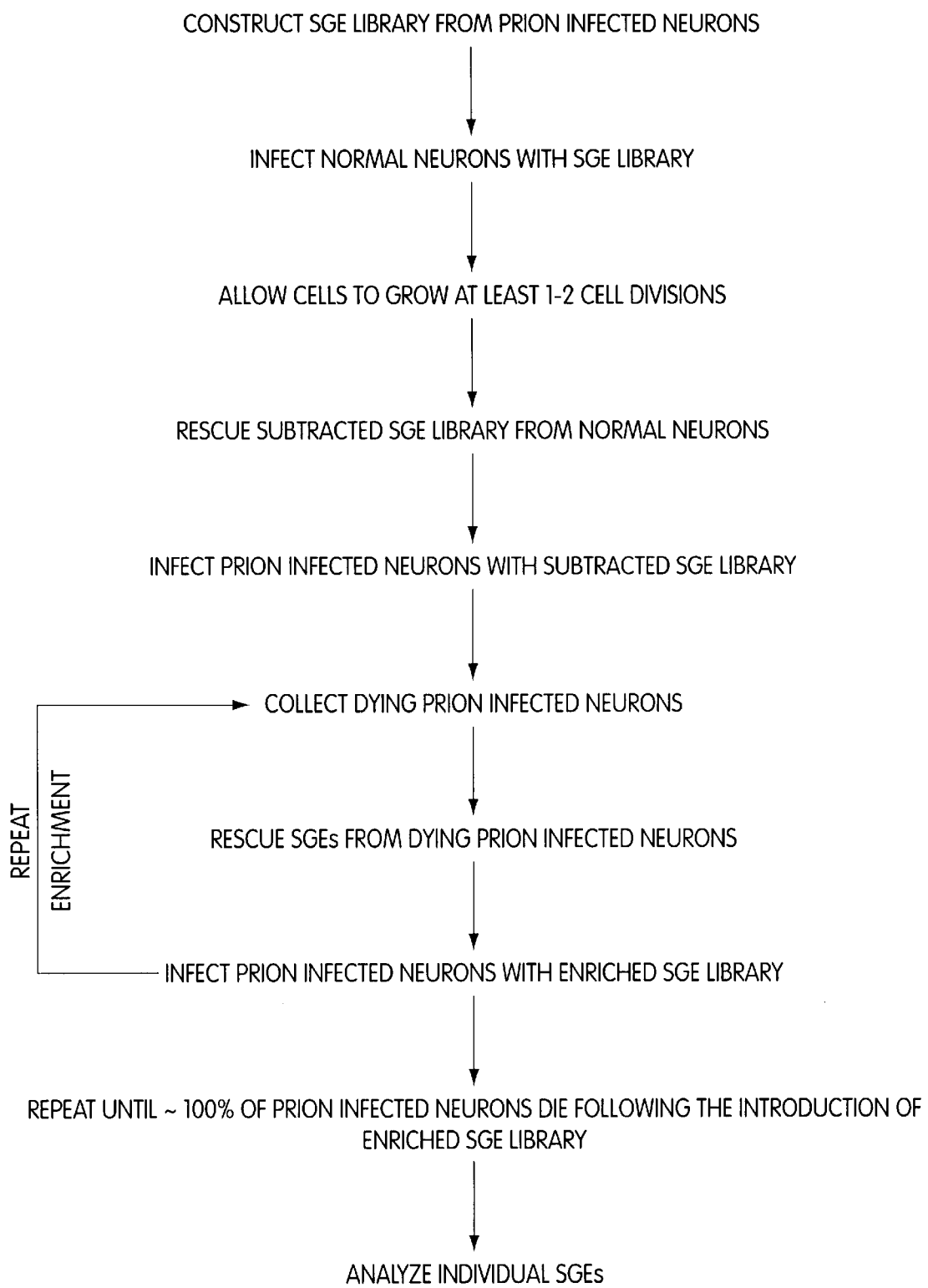

FIG. 8 depicts a therapeutic approach to isolate SGEs which selectively kill prion infected neurons. For this application the SGE library is constructed from prion-infected neurons. This variegated SGE library is introduced into normal neurons (subtractor cells) in order to subtract the normal lethal SGEs from the library. The subtracted SGE library is than introduced into prion-infected neurons (target cells) and dying cells are collected. The SGEs rescued from the dying cells are reintroduced into prion-infected neurons and dying cells are collected. This cycle is continued until ~100% of the prion-infected cells die following the introduction of the enriched SGE library. These SGEs identify genes whose function is essential for the survival of prion-infected cells but not essential for the survival of normal cells.

In addition to being a method for isolating SGEs that are themselves antiproliferative, as described above, the subject method can be carried out in a manner designed to identify SGEs which, rather than being acutely lethal themselves, confer an increased sensitivity to another agent, e.g., a cytotoxic agent. Identification of SGEs which selectively increase the sensitivity of a tumor cell to a chemotherapeutic agent is desirable.

In an illustrative embodiment, the chemotherapeutic agent is added to target cell culture and, optionally, the subtractive cell culture. Upon additions of the chemotherapeutic agent to the subtractive cell culture, cells that are isolated are those that express an SGE and survive beyond, e.g. the $T_{1/2}$ for the untransfected subtractive cells in the presence of the chemotherapeutic agent. Likewise, in the target cell culture, cells are isolated that are killed in some period of time less than the $T_{1/2}$ for the untransfected target cells. For example, isolating the cell populations which would undergo apoptosis with a $T_{1/2}$ of 1 or 2 $\sigma$ less than the $T_{1/2}$ for the untransfected cells should be enriched for SGEs which increase the sensitivity of the target cells for the chemotherapeutic agent.

iv. Druz Screening Assays

Another aspect of the invention is directed to the identification of agents capable of selectively modulating the phenotype of a cell, particularly the target cell or similar cells. For example, the subject method contemplates that agents can be developed which mimic the effect and selectivity of the identified SGE on the growth state of cells, e.g., of differentiation and proliferation, by targeting the endogenous gene or gene product (the "target gene" and "target gene product") which corresponds to the identified SGE. These agents include, but are not limited to, compounds that either potentiate or inhibit an intrinsic enzymatic activity of a target gene product or a complex including a target gene product, compounds that interfere with the interaction of a target gene product with other protein(s) or nucleic acid, and compounds comprising forms of a target gene product that are altered (mutated) to provide dominant loss-of-function or gain-of-function activity. The particular activity will depend on the characteristics of the target gene and/or target gene product identified in the subject method.

Potential targets identified by the screen:
1. Known "drugable" targets: known biochemical entities immediately "assayable": known enzyme/substrate pairs, appropriate for HTS
   known chemistry
2. Unknown but "drugable": target not known but sequence suggest biochemical activity
   not immediately assayable/no known substrate
   known chemistry
3. "Non-drugable": no obvious biochemical activity
   not "assayable"
   no chemistry
   can be used in gene therapy In this regard, the present invention provides assays for identifying agents that are either agonists or antagonists of the normal cellular function of a target gene product, or of the role of that target gene product in the pathogenesis of normal or abnormal cellular function such as proliferation and/or differentiation, and disorders related thereto. Compounds identified by the present assay can be used, for example, in the treatment of such disorders.

Agents to be tested for their ability to act as agonists or antagonists of a target gene product can be produced, for example, by bacteria, yeast or other organisms (e.g., natural products), produced chemically (e.g., small molecules, including peptidomimetics), or produced recombinantly. In a preferred embodiment, the test agent is a small organic molecule having a molecular weight of less than about 2,000 daltons. A high-speed screen for agents that bind directly to the target gene product may employ immobilized or "tagged" combinatorial libraries (or libraries which otherwise readily deconvoluted) of, e.g., small organic molecules.

Agents that are identified as active in the drug screening assay are candidates to be tested for their capacity to effect whole cells or tissue in vitro or in vivo.

A variety of assay formats will suffice and, in light of the present disclosure, those not expressly described herein will nevertheless be comprehended by one of ordinary skill in the art. For instance, the assay can be generated in many different formats, and include assays based on cell-free systems, e.g. purified proteins or cell lysates, as well as cell-based assays which utilize intact cells. Simple binding assays can also be used to detect agents which, such as those which detect compounds able to potentiate or disrupt protein-protein or protein-DNA interaction involving a target gene product or target gene.

In many drug screening programs which test libraries of compounds and natural extracts, high throughput assays are desirable in order to maximize the number of compounds surveyed in a given period of time. Assays of the present invention that are performed in cell-free systems, such as may be derived with purified or semi-purified proteins or with lysates, are often preferred as "primary" screens in that they can be generated to permit rapid development and relatively easy detection of an alteration in a molecular target that is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

Accordingly, in an exemplary screening assay of the present invention, a reaction mixture is generated to include a "target protein" (e.g., one form of a target gene product), test compound(s), and a "binding partner", e.g., a protein or nucleic acid which interacts with the target protein or that is a substrate of an enzymatic activity of the target protein. Detection and quantification of interaction, or substrate conversion (as appropriate) of the target protein with the binding partner provides a means for determining a compound's efficacy at inhibiting or potentiating interaction between the target protein and the binding partner. The efficacy of the compound can be assessed by generating dose response curves from data obtained using various concentrations of the test compound. Moreover, a control assay can also be performed to provide a baseline for comparison. In the control assay, interaction of the target protein and binding partner is quantitated in the absence of the test compound.

Interaction between the target protein and the binding partner may be detected by a variety of techniques. Modulation of the formation of complexes can be quantitated using, for example, detectably labeled proteins such as radiolabelled, fluorescently labeled, or enzymatically labeled target proteins, by immunoassay, by chromatographic detection, or by detecting the intrinsic activity of the acetylase.

Typically, it will be desirable to immobilize either the target protein or the binding partner to facilitate separation of complexes from uncomplexed forms of one or both of the proteins, as well as to accommodate automation of the assay. Binding of target protein to the binding partner, in the presence and absence of a candidate agent, can be accomplished in any vessel suitable for containing the reactants. Examples include microtiter plates, test tubes, and microcentrifuge tubes. In one embodiment, a fusion protein can be provided which adds a domain that allows the protein to be bound to a matrix. For example, glutathione-S-transferase/target protein (GST/target protein) fusion proteins can be adsorbed onto glutathione sepharose beads (Sigma Chemical, St. Louis, Mo.) or glutathione-derivatized microtitre plates, that are then combined with the cell lysates, e.g., an $^{35}$S-labeled, and the test compound, and the mixture incubated under conditions conducive to complex formation, e.g., at physiological conditions for salt and pH, though slightly more stringent conditions may be desired. Following incubation, the beads are washed to remove any unbound label, and the matrix immobilized and radiolabel determined directly (e.g., beads placed in scintillant), or in the supernatant after the complexes are subsequently dissociated. Alternatively, the complexes can be dissociated from the matrix, separated by SDS-PAGE, and the level of binding partner found in the bead fraction quantitated from the gel using standard electrophoretic techniques.

Other techniques for immobilizing proteins and other molecules on matrices are also available for use in the subject assay. For instance, either the target protein or binding partner can be immobilized utilizing conjugation of biotin and streptavidin. For instance, biotinylated target protein molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemical). Alternatively, antibodies reactive with the target protein, but which do not interfere with the interaction between the target protein and binding partner, can be derivatized to the wells of the plate, and the target protein trapped in the wells by antibody conjugation. As above, preparations of an binding partner and a test compound are incubated in the target protein-presenting wells of the plate, and the amount of complex trapped in the well can be quantitated. Exemplary methods for detecting such complexes, in addition to those described above for the GST-immobilized complexes, include immunodetection of complexes using antibodies reactive with the binding partner, or that are reactive with the target protein and compete with the binding partner; as well as enzyme-linked assays which rely on detecting an enzymatic activity associated with the target protein or binding partner, either intrinsic or extrinsic activity. In the instance of the latter, the enzyme can be chemically conjugated or provided as a fusion protein with the target protein or binding partner. To illustrate, the binding partner can be chemically cross-linked or genetically fused (if it is a polypeptide) with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating proteins trapped in the complex, antibodies against the protein, such as anti-target protein antibodies, can be used. Alternatively, the protein to be detected in the complex can be "epitope tagged" in the form of a fusion protein which includes, in addition to the target protein sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, N.J.).

An exemplary drug screening assay of the present invention includes the steps of (a) forming a reaction mixture including: (i) a binding partner, (ii) a target protein, and (iii) a test compound; and (b) detecting interaction of the binding partner and target protein. A statistically significant change (potentiation or inhibition) in the interaction of the target protein in the presence of the test compound, relative to the interaction in the absence of the test compound, indicates a potential agonist (mimetic or potentiator) or antagonist (inhibitor) for the test compound. The reaction mixture can be a cell-free protein preparation, e.g., a reconsistuted protein mixture or a cell lysate, or it can be a recombinant cell including a heterologous nucleic acid recombinantly expressing the target protein.

Where the target protein is a receptor, or participates as part of an oligomeric receptor complex, e.g., which complex includes other protein subunits, the cell-free system can be, e.g., a cell membrane preparation, a reconstituted protein mixture, or a liposome reconstituting the receptor. For instance, the protein subunits of a receptor complex including the target protein can be purified from detergent extracts from both authentic and recombinant origins can be reconstituted in artificial lipid vesicles (e.g., phosphatidylcholine liposomes) or in cell membrane-derived vesicles (see, for example, Bear et al. (1992) Cell 68:809–818; Newton et al. (1983) Biochemistry 22:6110–6117; and Reber et al. (1987) J Biol Chem 262:11369–11374). The lamellar structure and size of the resulting liposomes can be characterized using electron microscopy. External orientation of the receptor in the reconstituted membranes can be demonstrated, for example, by immunoelectron microscopy. The interaction of a ligand or test compound with liposomes containing such target protein complexes and liposomes without the protein can be compared in order to identify potential modulators of the receptor.

In yet another embodiment, the drug screening assay is derived to include a whole cell expressing a target protein. The ability of a test agent to alter the activity of the target protein can be detected by analysis of the recombinant cell. For example, agonists and antagonists of the target protein biological activity can by detected by scoring for alterations in growth or differentiation (phenotype) of the cell. General techniques for detecting each are well known, and will vary with respect to the source of the particular reagent cell utilized in any given assay. For the cell-based assays based on target genes identified in human cells, the recombinant cell is preferably a metazoan cell, e.g., a mammalian cell, e.g., an insect cell, e.g., a xenopus cell, and may be an adult cell, an embryonic cell, or an oocyte. In other embodiments, where the target protein is a receptor, the receptor can be reconstituted in yeast or bacterial cells.

In addition to morphological studies, change(s) in the level of an intracellular second messenger responsive to activities dependent on the target protein can be detected. For example, in various embodiments the assay may assess the ability of test agent to cause changes in phophorylation patterns, adenylate cyclase activity (cAMP production), GTP hydrolysis, calcium mobilization, and/or phospholipid hydrolysis ($IP_3$, DAG production). By detecting changes in intracellular signals, such as alterations in second messengers or gene expression, candidate agonists and antagonists to target protein-dependent signaling can be identified.

Target proteins may regulate the activity of phospholipases. Inositol lipids can be extracted and analyzed using standard lipid extraction techniques. Water-soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be dependent on a target protein. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of $Ca^{++}$ detection, cells could be loaded with the $Ca^{++}$-sensitive fluorescent dye fura-2 or indo-1, using standard methods, and any change in $Ca^{++}$ measured using a fluorometer.

In certain embodiments of the assay, it may be desirable to screen for changes in cellular phosphorylation. The ability of compounds to modulate serine/threonine kinase or tyrosine kinase activation could be screened using colony immunoblotting (Lyons and Nelson (1984) *PNAS* 81:7426–7430) using antibodies against phosphorylated serine, threonine or tyrosine residues. Reagents for performing such assays are commercially available, for example, phosphoserine and phosphothreonine specific antibodies which measure increases in phosphorylation of those residues can be purchased from commercial sources.

Certain of the target protein may set in motion a cascade involving the activation and inhibition of downstream effectors, the ultimate consequence of which is, in some instances, a detectable change in the transcription or translation of a gene. By selecting transcriptional regulatory sequences from such target genes, e.g., that are responsible for the up- or down-regulation of these genes, and operatively linking such promoters to a reporter gene, the present invention provides a transcription-based assay that is sensitive to the ability of a specific test compound to influence signalling pathways dependent on the target protein.

In an exemplary embodiment, the subject assay comprises detecting, in a cell-based assay, change(s) in the level of expression of a gene controlled by a transcriptional regulatory sequence responsive to signaling by a target protein. Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on signaling by the target protein. Expression of the reporter gene, thus, provides a valuable screening tool for the development of compounds that act as agonists or antagonists of target protein-dependent signalling.

In practicing one embodiment of the assay, a reporter gene construct is inserted into the reagent cell in order to generate a detection signal dependent on second messengers generated by the target protein. Typically, the reporter gene construct will include a reporter gene in operative linkage with one or more transcriptional regulatory elements responsive to signal transduction from the target protein, with the level of expression of the reporter gene providing the detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound or it may be compared with the amount of transcription in a substantially identical cell that lacks the target receptor protein. Any statistically or otherwise significant difference in the amount of transcription indicates that the test compound has in some manner altered the inductive activity of the target protein.

As described in above, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug. Many reporter genes are known to those of skill in the art and others may be identified or synthesized by methods known to those of skill in the art. A reporter gene includes any gene that expresses a detectable gene product, that may be RNA or protein.

In still another embodiment of a drug screening, a two hybrid assay can be generated with a target protein and binding partner. Drug dependent inhibition or potentiation of the interaction can be scored. The two hybrid assay formats described in the art can be readily adaoted for such drug screening embodiments. See, for example, U.S. Pat. Nos. 5,283,317, 5,580,736 and 5,695,941; Zervos et al. (1993) Cell 72:223–232; Madura et al. (1993) J Biol Chem 268:12046–12054; Bartel et al. (1993) Biotechniques 14:920–924; and Iwabuchi et al. (1993) Oncogene 8:1693–1696)

In addition to small molecules that may be identified, e.g., by the drug screening assays described above, other agents capable of modulating the activity of the target gene product may include peptide domains (fragments) of the target protein. A "mutant" as used herein refers to a peptide having an amino acid sequence which differs from that of the naturally occurring peptide or protein by at least one amino acid. Mutants may have the same biological and immunological activity as the naturally occurring protein. However, the biological or immunological activity of mutants may differ or be lacking. For example, a protein mutant may act as an agonist, antagonist (competitive or non-competitive), or partial agonist of the function of the naturally occurring protein.

For example, homologs of the target proteins (both agonist and antagonist forms) can be generated using, for example, alanine scanning mutagenesis and the like (Ruf et al. (1994) Biochemistry 33:1565–1572; Wang et al. (1994) J. Biol. Chem. 269:3095–3099; Balint et al. (1993) Gene 137:109–118; Grodberg et al. (1993) Eur. J. Biochem. 218:597–601; Nagashima et al. (1993) J. Biol. Chem. 268:2888–2892; Lowman et al. (1991) Biochemistry 30:10832–10838; and Cunningham et al. (1989) Science 244:1081–1085), by linker scanning mutagenesis (Gustin et al. (1993) Virology 193:653–660; Brown et al. (1992) Mol.

Cell Biol. 12:2644–2652; McKnight et al. (1982) Science 232:316); by saturation mutagenesis (Meyers et al. (1986) Science 232:613); by PCR mutagenesis (Leung et al. (1989) Method Cell Mol Biol 1:11–19); or by random mutagenesis (Miller et al. (1992) A Short Course in Bacterial Genetics, CSHL Press, Cold Spring Harbor, N.Y.; and Greener et al. (1994) Strategies in Mol Biol 7:32–34). Linker scanning matagenesis, particularly in a combinatorial setting, is on attractive method for identifying truncated (such as constitutively active or dominant negative) forms of a target protein.

The invention also contemplates the reduction of the subject target protein to generate mimetics, e.g., peptide or non-peptide agents, that are able interfere with., or mimic, the effect of the authentic target protein on the cells. Such peptidomimetics can act as drugs for the modulation of smooth cell differentiation.

Peptidomimetics are commonly understood in the pharmaceutical industry to include non-peptide drugs having properties analogous to those of the mimicked peptide. The principles and practices of peptidomimetic design are known in the art and are described, for example, in Fauchere, *Adv. Drug Res.* 15:29 (1986); and Evans et al., *J. Med. Chem.* 30:1229 (1987). Peptidomimetics which bear structural similarity to therapeutically useful peptides may be used to produce an equivalent therapeutic or prophylactic effect. Typically, such peptidomimetics have one or more peptide linkages optionally replaced by a linkage that may convert desirable properties such as resistance to chemical breakdown in vivo. These linkages may include —$CH_2NH$—, —$CH_2S$—, —$CH_2$—$CH_2$—, —$CH=CH$—, —$COCH_2$—, —$CH(OH)CH_2$—, and —$CH_2SO$—. Peptidomimetics may exhibit enhanced pharmacological properties (biological half life, absorption rates, etc.), different specificity, increased stability, production economies, lessened antigenicity and the like which makes their use as therapeutics particularly desirable.

Such mutagenic techniques as described above are also particularly useful for mapping the determinants of a target proteins which participate in protein-protein interactions. To illustrate, the critical residues of a target protein that are involved in molecular recognition of other cellular proteins (or nucleic acid) can be determined and used to generate peptidomimetics which maintain at least a portion of that binding activity. By employing, for example, scanning mutagenesis to map the amino acid residues involved in binding, peptidomimetic compounds (e.g., diazepine or isoquinoline derivatives) can be generated which mimic those residues in binding to the kinase. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J. Med. Chem.* 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) *Biochem Biophys Res Commun* 126:419; and Dann et al. (1986) *Biochem Biophys Res Commun* 134:71).

Modulation of the activity of a target gene according to the invention includes methods employing specific antisense polynucleotides complimentary to all or part of the nucleotide sequences encoding peptide domains comprising the target protein or antisense polynucleotides complimentary to all or part of the 3' or 5' noncoding regions of the target gene. Such complimentary antisense polynucleotides may include nucleotide additions, deletions, substitutions and transpositions, providing that specific hybridization to the target sequence persists.

As used herein, "antisense" therapy refers to administration or in situ generation of oligonucleotide probes or their derivatives which specifically hybridize (e.g., bind) under cellular conditions with cellular mRNA and/or genomic DNA encoding a target protein. The hybridization should inhibit expression of that protein, e.g., by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

Soluble antisense RNA or DNA oligonucleotides which can hybridize specifically to mRNA species encoding proteins comprising the molecular regulators, and which prevent transcription of the mRNA species and/or translation of the encoded polypeptide are contemplated as complimentary antisense polynucleotides according to the invention.

An antisense construct of the present invention can be delivered, for example, as an expression plasmid which, when transcribed in the cell, produces RNA that is complementary to at least a unique portion of the target cellular mRNA. Alternatively, the antisense construct is an oligonucleotide probe that is generated ex vivo and which, when introduced into the cell causes inhibition of expression by hybridizing with the mRNA and/or genomic sequences of a target gene. Such oligonucleotide probes are preferably modified oligonucleotide that are resistant to endogenous nucleases, e.g. exonucleases and/or endonucleases, and is therefore stable in vivo. Exemplary nucleic acid molecules for use as antisense oligonucleotides are phosphoramidate, phosphorothioate and methylphosphonate analogs of DNA (see also U.S. Pat. Nos. 5,176,996; 5,264,564; and 5,256, 775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26-mers. When testing an antisense oligonucleotide, a mismatched control can be constructed. The controls can be generated by reversing the sequence order of the corresponding antisense oligonucleotide in order to conserve the same ratio of bases.

Computer-aided molecular modeling of the target proteins can be used to study three-dimensional structures using computer visualization techniques. Novel designs of low molecular weight inhibitors or oligopeptides can then be analyzed for selective inhibition. Descriptions of targeted drug design can be found in Kuntz, "Structure-Based Strategies for Drug Design and Discovery," *Science* 257:1078–1082 (1992) and Dixon, "Computer-Aided Drug Design: Getting the Best Results," *Trends in Biotechnology*, 10:357–363 (1992). Specific applications of the binding of inhibitors to targets using computer modeling have been described in Piper et al., "Studies Aided by Molecular Graphics of Effects of Structural Modifications on the Binding of Antifolate Inhibitors to Human Dihydrofolate Reductase," *Proc. Am. Assoc. Cancer Res. Annual Meeting*, 33:412 (1992); Hibert et al., "Receptor 3D-Models and Drug Design," *Therapie* (Paris), 46:445–451 (1991)(serotonin receptor recognition sites). Computer programs that can be used to conduct three-dimensional molecular modeling are described in Klopman, "Multicase 1: A Hierarchical Computer Automated Structure Evaluation Program," *Quantitative Structure-Activity Relationships*, 11:176–184 (1992); Pastor et al., "The Edisdar Programs Rational Drug Series Design," *Quantitative Structure-Activity Relationships*, 10:350–358 (1991); Bolis et al., "A Machine Learning Approach to Computer-Aided Molecular Design," *J. Computer Aided Molecular Design*, 5:617–628 (1991); and Lawrence and Davis, "CLIX: A Search Algorithm for Finding Novel Ligands Capable of Binding Proteins of Known Three-Dimensional Structure," *Proteins Structure Functional Genetics*, 12:31–41 (1992).

In still other embodiments, low molecular weight inhibitors specific for the molecular regulators can be predicted by molecular modeling and synthesized by standard organic chemistry techniques. Computer modeling can identify oligopeptides which enhance the smooth muscle cell differentiation or block their dedifferentiation. Techniques for producing the identified oligopeptides are well known and can proceed by organic synthesis of amino acids, by genetic engineering techniques, or by PCR based amplification. Silverman, *The Organic Chemistry of Drug Design and Drug Action*, Academic Press (1992). The inhibitors of this invention can be identified as those inhibitors that selectively inhibit the smooth muscle cell dedifferentiation.

v. Pharmaceutical Preparations of Identified Agents

After identifying certain test SGEs, or compounds identified from the drug screening assays described above, the practitioner of the subject assay will continue to test the efficacy and specificity of the selected agents both in vitro and in vivo. Whether for subsequent in vivo testing, or for administration to an animal as an approved drug, SGEs and other compounds identified in the subject assays can be formulated in pharmaceutical preparations for in vivo administration to an animal, preferably a human. SGEs that are active as polypeptides can be turned into peptidomimetics. Likewise, antisense SGEs can be generated as non-hydrolizable analogs (e.g., resistant to nuclease degradation) and formulated for direct administration, or, as appropriate, provided in the form of an expression vector, such as for gene therapy, which produces the antisense molecule as a transcript. SGEs that are active as polypeptides can also be provided in the form of an expression vector for use, e.g., in gene therapy.

The peptides, proteins and antisense selected in the subject assay, or gene therapy vectors encoding such molecules, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like that may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the SGE compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

vi. Exemplification

To determine the efficiency at which cDNAs that direct apoptosis are recovered from dying cells captured from a population of proliferating cells using our assays, the following experiments were performed.

HT1080/EcoR/TR cells (TR9) expressing a retroviral construct that carries the death-inducing cDNA p53 (TR9/pKK121) were mixed with cells expressing the LacZ control (TR9/pLXI-3) at known ratios. The retroviral vector in these constructs (pIC762) permits both regulation of transgene expression (conditional induction by doxycycline) and participation in retroviral cloning cycles (i.e., recovery by in vitro recombination, amplification in *E. Coli* and generation of infectious retrovirus particles for subsequent target cell infections).

A total of $2 \times 10^5$ cells were seeded onto each 10 cm tissue culture dish. Doxycycline was added the next day at 1 g/ml. Apoptotic cells were harvested 48 hours after the addition of doxycycline by one of two methods, 'Annexin Sort' or 'Floaters'.

In the first case, adherent cells were detached by trypsinization, washed, incubated with annexin-FITC and propidium iodide (AnnexinV-FITC kit, Calbiochem) and sorted by FACS (MoFlo sorter, Cytomation). Early apoptotic, Annexin V-FITC labelled cells were collected.

In the second case, dying cells were simply collected from the supernatant by centrifugation. Genomic DNA was prepared from the cells captured by both methods and resus pended in 20 1 of dH₂O. 10 μl were used in an in vitro recombination (excision) reaction using the KW recombinase that converts the linear, integrated retrovirus into circular proviral plasmid form. The excision mix was electroporated into DH10b/trfA cells and plated onto LB agar plates containing 50 μg/ml Zeocin and the chromogenic substrate Xgal. Bacterial colonies harboring the LacZ proviral construct were identified by their blue color. Those containing the p53 proviral construct were identified both by their white color and by PCR with p53-specific oligos MIC490 and MIC491. The enrichment factor for each capture was determined by taking the ratio of p53 to LacZ bacterial colonies divided by the initial ratio of p53 to LacZ TR9 cells at seeding. For example, in the table below, 4 white p53 colonies and 22 blue LacZ colonies were obtained from cells initially seeded at 1:1000 and captured by the annexin sort procedure, yielding an enrichment factor of 180.

| Initial Cells p53: LacZ | Annexin Sort Excisants Recovered Fold Enrichment | Floaters Excisants Recovered Fold Enrichment |
|---|---|---|
| 1:1 | ~10 | 5 |
| 1:10 | 2 | 3 |
| 1:100 | 60 | 290 |
| 1:1000 | 180 | 4,000 |
| 1:10,000 | 5,000 | — |
| 1:100,000 | 2,000 | — |

Both procedures lead to significant enrichment of the apoptosis-inducing p53 construct over the LacZ control after one cycle of induction, particularly at dilutions greater or equal to 1:1,000. This experiment demonstrates the feasibility of isolating rare apoptotic cells from large cell populations and the rescue of apoptosis-causing retroviral constructs from the dying cells.

Induction of Apoptosis by Antisense HDM2 Fragment

Human MDM2 (HDM2) is a negative regulator of the p53 tumor suppressor. Antisense oligodeoxynucleotides that inhibit MDM2 have been shown to activate p53 function and in some cell lines, lead to apoptosis (Chen et al. (1999) Molecular Medicine 5: 21–34).

The following experiment was conducted to determine whether a specific fragment of HDM2 cDNA, when expressed in the antisense orientation from a retroviral vector can induce apoptosis in HT1080. This cDNA fragment encompasses the sequence from which the antisense oligonucleotides reported in the above paper derive.

A fragment of HDM2 from nucleotides 259 to 465, was PCR amplified and cloned in the antisense orientation into the retroviral vector pIC762 using BamHI and XhoI sites (pKKI19). The expression of the fragment is induced by the addition of doxycycline. HT1080/EcoR/TR cells were infected with pKKI 19 retrovirus. Puromycin-resistant infected cells were tested for their ability to induce cell death upon expression of the antisense in two separate assays.
1) Colony Formation Assay: 10E5, 10E4, 10E3 and 100 cells were each seeded two parallel series of 10 cm tissue culture plates, in medium containing 1 μg/ml doxycycline, or not. After 14 days of incubation, the colonies were visualized by staining with crystal violet and counted. Cells expressing a GFP cDNA in the same vector served as control.

Number of Colonies

| | AS HDM2 fragment | | GFP cDNA | |
|---|---|---|---|---|
| Cells seeded | No Dox | +Dox 1 μg/ml | No Dox | +Dox 1 μg/ml |
| 10⁵ | ~500 | ~10 | ~500 | ~500 |
| 10⁴ | ~10 | 0 | ~24 | 30 |
| 10³ | 0 | 0 | 3 | 1 |
| 10² | 0 | 0 | 0 | 0 |

Figure 9:
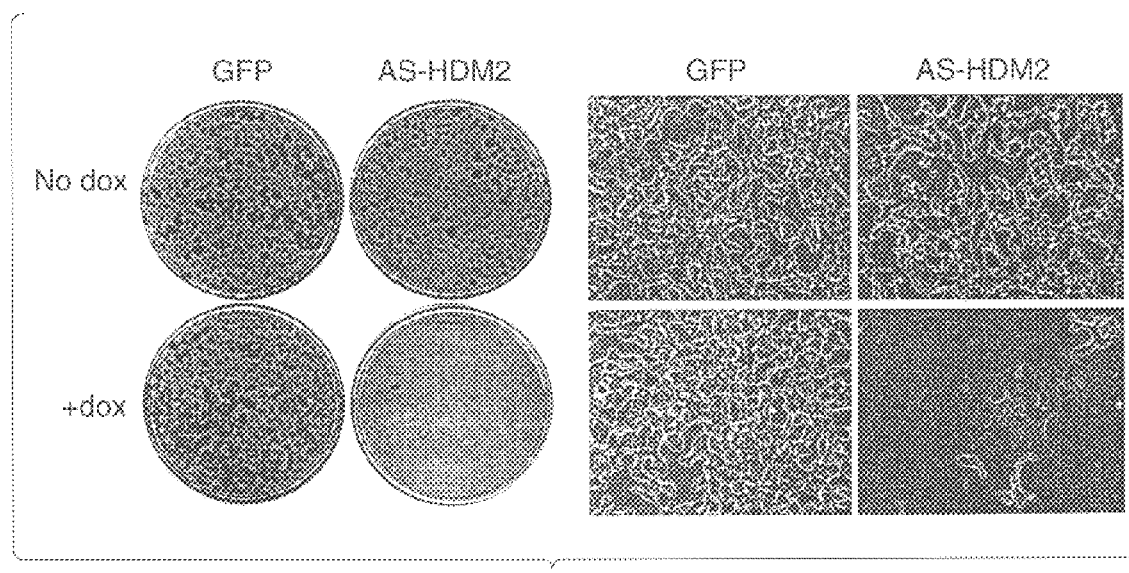
FIG. 9 depicts results of a colony-formation assay as described below.

At least a 50-fold difference was observed between the number of colonies formed in the presence and absense of doxycycline. By contrast, cells expressing the control GFP cDNA showed no significant difference between the doxycyline-treated or untreated samples. These results suggest that induction of the antisense HDM2 construct leads to decreased viability of the cells, presumably by p53-induced apoptosis (see FIG. 9).

Figure 10:
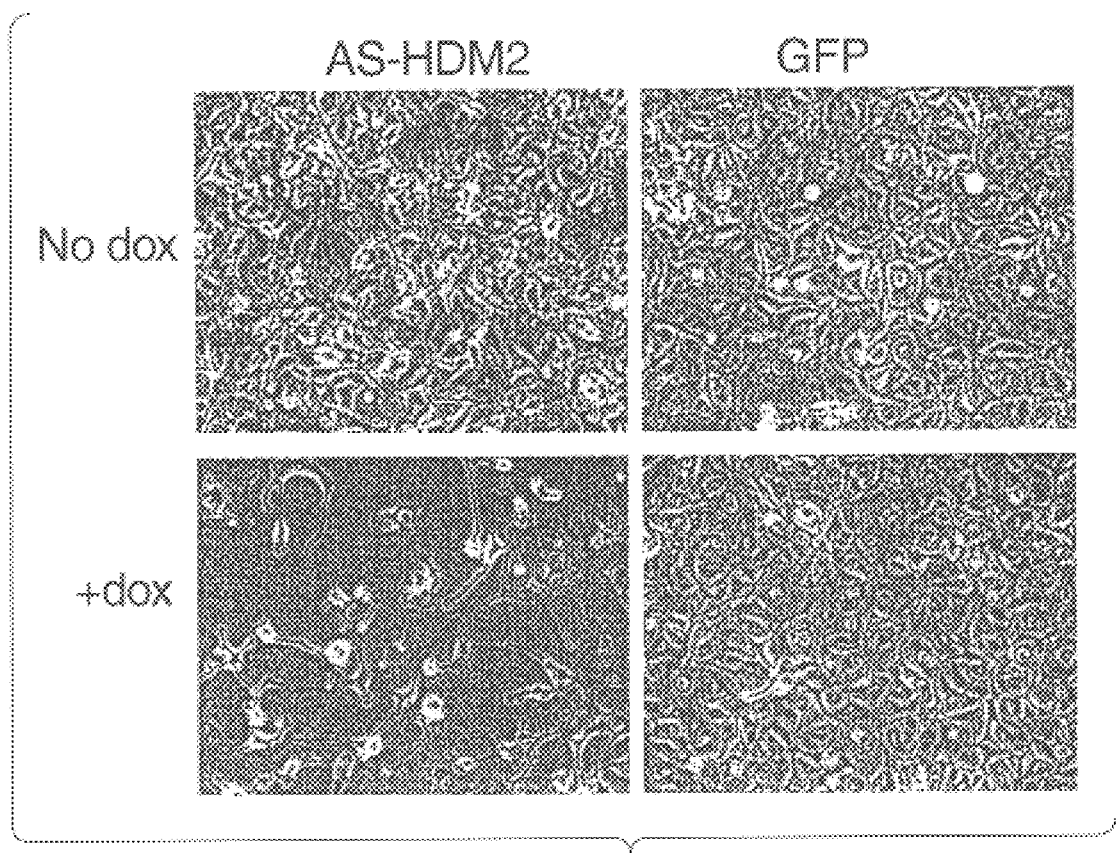
FIG. 10 presents results of an experiment indicating that expression of AS-HDM2 induces cell death.

2) Microscopic Examination: 2×10⁵ cells were seeded in each of two 10 cm plates. The next day, 1 μg/ml doxycyline was added to one plate. Cells were examined after 5 days. Significantly fewer cells were attached and many more cells were floating in the plate containing doxycycline compared to the one without, consistent with the interpretation that expression of the HDM2 antisense construct induces cell death (see FIG. 10).

Expression of an antisense fragment of HDM2 can lead to death, presumably via activation of p53-induced apoptosis. This suggests the feasibility of isolating antisense fragments of cellular genes whose expression induces tumor cell death.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying agents with selective antiproliferative activity for a target cell that proliferates abnormally, comprising:
   (i) transfecting subtractive cells that proliferate normally do not express a recombinat reporter gene with a library of expression vectors comprising a variegated population of coding sequences for potential synthetic genetic elements (SGEs);
   (ii) identifying viable cells from among the transfected subtractive cells;
   (iii) isolating from the identified viable cells those SGE vectors of the SGE library that are not antiproliferative to the subtractive cells;
   (iv) transfecting target cells that proliferate abnormally and do not express a recombinant report gene with the SGE vectors isolated in step (iii);
   (v) identifying non-viable cells from among the transfected target cells; and
   (vi) isolating from the identified cells those SGE vectors with selective antiproliferative activity for the target cell.

2. The method of claim 1, wherein the target and subtractive cells are eukaryotic cells.

3. The method of claim 2, wherein the target and subtractive cells are eukaryotic cells.

4. The method of claim 2, wherein at least one of the target and subtractive cells are human cells.

5. The method of claim 1, wherein the target cell is a transformed cell, and subtractive cell is an untransformed cell.

6. The method of claim 5, wherein the subtractive cells are untransformed cells of the same type from which the transformed target cells are derived.

7. The method of claim 1, wherein the target cell is infected by a virus, and subtractive cell is a cell not infected with the virus.

8. The method of claim 1, wherein the expression vectors are viral vectors.

9. The method of claim 8, wherein the viral vectors are retroviral vectors.

10. The method of claim 1, wherein the SGE library is generated from a normalized cDNA library.

11. The method of claim 1, wherein the SGE library is generated from a subtractive cDNA library.

12. The method of claim 1, wherein the SGE is a sense-oriented sequence encoding a peptide.

13. The method of claim 12, further comprising
   (vii) synthesizing a peptidomimetic analog of a peptide encoded by one or more SGEs isolated in step (vi).

14. The method of claim 1, wherein the SGE is an antisense-oriented sequence encoding an antisense RNA.

15. The method of claim 1, wherein identifying non-viable cells includes identifying cells in the process of undergoing apoptosis.

16. A method for identifying agents which selectively confer a desired phenotype on a target cell, comprising:
   (i) transfecting subtractive cells which do not express recombinant reporter gene with a library of expresssion vectors comprising a variegated population of coding sequences for potential synthetic genetic elements (SGEs);
   (ii) identifying cells from the transfected subtractive cells that do not have the desired phenotyhpe and do not have a phenotype which interferes with the detection of the desired phenotype;
   (iii) isolating, from the identified cells, those SGE vectors of the SGE library which transfected the identified cells;
   (iv) transfecting target cells which do not express a recombinant reporter gene with the subpopulation of SGE vectors isolated in step (iii);
   (v) identifying cells that have the desired phenotype from among the transfected target cell; and
   (vi) isolating those SGC vectors which confer the desired phenotype to the target cell.

17. The method of claim 16, further comprising
   (vii) formulating a preparation comprising an excipient and one or more SGEs isolated in-step (vi).

18. The method of claim 16, wherein the desired phenotype is lethal to the target cell.

19. A method for identifying agents with selective antiproliferative activity for a target cell that proliferates abnormally, comprising:
   (i) transfecting target cells that proliferate abnormally and do not express a recombinant reporter gene with a library of expression vectors comprising a variegated population of coding sequences for potential synthetic genetic elements (SGEs);
   (ii) identifying non-viable cells from among the transfected target cells;
   (iii) isolating from the identified cells those SGE vectors with selective antiproliferative activity for the target cell;
   (iv) transfecting subtractive cells that proliferate normally and do not express a recombinant reporter gene with the SGE vectors isolated in step (iii);
   (v) identifying viable cells from among the transfected subtractive cells; and
   (vi) isolating from the identified cells those SGE vectors of the SGE library that are not antiproliferative to the subtractive cells.

20. The method of claim 19, wherein the target and subtractive cells are eukaryotic cells.

21. The method of claim 20, wherein the target and subtractive cells are mammalian cells.

22. The method of claim 20, wherein at least one of the target and subtractive cells are human cells.

23. The method of claim 19, wherein the target cells are transformed cells, and the subtractive cells are untransformed cells.

24. The method of claim 23, wherein the subtractive cells are untransformed cells of the same type from which the transformed target cells are derived.

25. The method of claim 19, wherein the target cell is infected by a virus, and subtractive cell is a cell not infected with the virus.

26. The method of claim 19, wherein the expression vectors are viral vectors.

27. The method of claim 26, wherein the viral vectors are retroviral vectors.

28. The method of claim 19, wherein the SGE library is generated from a normalized cDNA library.

29. The method of claim 19, wherein the SGE library is generated from a subtractive cDNA library.

30. The method of claim 19, wherein the SGE is a sense-oriented sequence encoding a peptide.

31. The method of claim 30, further comprising
   (vii) synthesizing a peptidomimetic analog of a peptide encoded by one or more SGEs isolated in step (vi).

32. The method of claim 19, wherein the SGE is an antisense-oriented sequence encoding an antisense RNA.

33. The method of claim 19, wherein identifying non-viable cells includes identifying cells in the process of undergoing apoptosis.

34. A method for identifying agents which selectively confer a desired phenotype on a target cell, comprising:
   (i) transfecting target cells which do not express a recombinant reporter gene with a library of expression vectors comprising a variegated population of coding sequences for potential synthetic genetic elements (SGEs);
   (ii) identifying cells that have the desired phenotype from among the transfected target cells;
   (iii) isolating from the identified cells those SGE vectors which confer the desired phenotype to the target cell;
   (iv) transfecting subtractive cells which do not express a recombinant reporter gene with the sub-population of SGE vectors isolated in step (iii);

(v) identifying cells from the transfected subtractive cells that do not have the desired phenotype and do not have a phenotype which interferes with the detection of the desired phenotype; and (vi) isolating, from the identified cells, those SGE vectors of the SGE library which transfected the identified cells.

35. The method of claim 34, further comprising (vii) formulating a preparation comprising an excipient and one or more SGEs isolated in step (vi).

36. The method of claim 34, wherein the desired phenotype is lethal to the target cell.

* * * * *

UNITED STATES PATENT AND TRADEMARK OFFICE
CERTIFICATE OF CORRECTION

PATENT NO. : 6,342,356 B1
DATED : January 29, 2002
INVENTOR(S) : Jeno Gyuris

Page 1 of 1

It is certified that error appears in the above-identified patent and that said Letters Patent is hereby corrected as shown below:

Column 30,
Line 50, insert -- and -- before "do not express" and replace "recombinat" with -- recombinant --.
Line 61, replace "report" with -- reporter --.

Column 31,
Line 4, replace "eukaryotic" with -- mammalian --.
Line 7, replace "cell is a" with -- cells are --.
Line 8, replace "cell, and subtractive cell is an" with -- cells, and the subtractive cells are --.
Line 9, replace "cell." with -- cells. --.
Line 13, replace "and subtractive cell is" with -- and the subtractive cells are --.
Line 14, replace "cell is a cell" with -- cells are cells --.
Line 36, insert -- a -- before "recombinant" and replace "expresssion" with -- expression --.
Line 41, replace "phenotyhpe" with -- phenotype --.
Line 52, replace "cell" with -- cells --.
Line 53, replace "SGC" with -- SGE --.
Line 54, replace "cell" with -- cells --.
Line 57, replace "in-step" with -- in step --.

Column 32,
Line 29, replace "cell is" with -- cells are --.
Line 30, replace "cell is a cell" with -- cells are cells --.

Signed and Sealed this

Fourteenth Day of May, 2002

Attest:

Attesting Officer

JAMES E. ROGAN
Director of the United States Patent and Trademark Office